(12) United States Patent
Samuels et al.

(10) Patent No.: US 10,272,229 B2
(45) Date of Patent: Apr. 30, 2019

(54) METHOD AND APPARATUS FOR ALLOWING INFLATION OF INFLATABLE ELEMENTS WITHIN MEDICAL DEVICES

(71) Applicant: EndoVention, Inc., San Francisco, CA (US)

(72) Inventors: Shaun Laurence Wilkie Samuels, Coral Gables, FL (US); Peter Yorke, San Francisco, CA (US)

(73) Assignee: Endovention, Inc., San Francisco, CA (US)

( * ) Notice: Subject to any disclaimer, the term of this patent is extended or adjusted under 35 U.S.C. 154(b) by 0 days.

(21) Appl. No.: 15/115,821

(22) PCT Filed: Apr. 20, 2016

(86) PCT No.: PCT/US2016/028324
§ 371 (c)(1),
(2) Date: Aug. 1, 2016

(87) PCT Pub. No.: WO2016/200490
PCT Pub. Date: Dec. 15, 2016

(65) Prior Publication Data
US 2018/0161553 A1    Jun. 14, 2018

Related U.S. Application Data

(60) Provisional application No. 62/174,252, filed on Jun. 11, 2015, provisional application No. 62/172,437, filed on Jun. 8, 2015.

(51) Int. Cl.
*A61M 31/00* (2006.01)
*A61M 25/10* (2013.01)
*A61F 2/01* (2006.01)

(52) U.S. Cl.
CPC .... *A61M 25/1018* (2013.01); *A61M 25/1002* (2013.01); *A61F 2/013* (2013.01);
(Continued)

(58) Field of Classification Search
CPC ...................... A61M 25/1018; A61M 25/1002
(Continued)

(56) References Cited

U.S. PATENT DOCUMENTS 2,248,934 A    7/1941   Auzin
2,854,983 A   10/1958   Baskin
(Continued)

OTHER PUBLICATIONS

Notification and International Search Report (PCT/ISA/210) corresponding to PCT/US16/28324 (3 pgs) dated Jul. 18, 2016.
(Continued)

*Primary Examiner* — Edelmira Bosques
(74) *Attorney, Agent, or Firm* — The Petruzzi Law Firm; James D. Petruzzi

(57) ABSTRACT

Embodiments of the present invention are directed to a rigid connector which joins an inflation lumen to an inflatable element in a medical device. The connector comprises a shaft fluidly connected to a crossbar. Preferably one embodiment provides a stable junction through which an inflation fluid may pass and inflate an inflatable element which is not co-linear with the axis of inflation. The junction maintains a generally rigid, fixed angle in relation to the axis of the inflation lumen, which in many embodiments is perpendicular to said axis. This fixed orientation creates a robust structure which is resistant to deflection when forces are encountered during its use within tubular and non-tubular structures within the human body. Such a structure maintains a rigid orientation between the inflatable element and the catheter body.

28 Claims, 19 Drawing Sheets

(52) U.S. Cl.
CPC ............... *A61F 2250/0003* (2013.01); *A61M 2025/1052* (2013.01)

(58) Field of Classification Search
USPC .................................. 604/103, 103.07, 284
See application file for complete search history.

(56) References Cited

U.S. PATENT DOCUMENTS

| | | | |
|---|---|---|---|
| 4,447,227 | A | 5/1984 | Kotsanis |
| 4,685,447 | A | 8/1987 | Iversen et al. |
| 5,322,519 | A | 6/1994 | Ash |
| 5,554,185 | A | 9/1996 | Block et al. |
| 5,662,671 | A | 9/1997 | Barbut et al. |
| 5,769,816 | A | 6/1998 | Barbut et al. |
| 5,908,435 | A | 6/1999 | Samuels |
| 5,947,995 | A | 9/1999 | Samuels |
| 5,954,745 | A | 9/1999 | Gertler et al. |
| 6,007,575 | A | 12/1999 | Samuels |
| 6,159,230 | A | 12/2000 | Samuels |
| 6,245,088 | B1 | 6/2001 | Lowery |
| 8,007,540 | B2 | 8/2011 | Robertson |
| 8,012,201 | B2 | 9/2011 | Lashinski et al. |
| 8,097,014 | B2 | 1/2012 | Borkon |
| 8,277,465 | B2 | 10/2012 | Beane et al. |
| 8,708,955 | B2 | 4/2014 | Tilson et al. |
| 8,932,326 | B2 | 1/2015 | Riina et al. |
| 8,945,169 | B2 | 2/2015 | Pal |
| 9,017,397 | B2 | 4/2015 | Osborne et al. |
| 2003/0125797 | A1 | 7/2003 | Chobotov et al. |
| 2006/0020327 | A1 | 1/2006 | Lashinski et al. |
| 2006/0020333 | A1 | 1/2006 | Lashinski et al. |
| 2006/0020334 | A1 | 1/2006 | Lashinski et al. |
| 2006/0025854 | A1 | 2/2006 | Lashinski et al. |
| 2006/0025855 | A1 | 2/2006 | Lashinski et al. |
| 2006/0223386 | A1 | 10/2006 | Pal |
| 2007/0185566 | A1 | 8/2007 | Khitin et al. |
| 2007/0270897 | A1 | 11/2007 | Skerven et al. |
| 2008/0086083 | A1 | 4/2008 | Towler |
| 2008/0154357 | A1 | 6/2008 | Shalev |
| 2008/0208329 | A1 | 8/2008 | Bishop et al. |
| 2009/0043368 | A1 | 2/2009 | Jung et al. |
| 2009/0270964 | A1 | 10/2009 | Huetter |
| 2009/0299327 | A1 | 12/2009 | Tilson et al. |
| 2010/0076484 | A1 | 3/2010 | Riina et al. |
| 2011/0172697 | A1 | 7/2011 | Jonsson |
| 2011/0213460 | A1 | 9/2011 | Lashinski et al. |
| 2012/0016468 | A1 | 1/2012 | Robin et al. |
| 2012/0022629 | A1 | 1/2012 | Perera et al. |
| 2012/0083819 | A1 | 4/2012 | Wang et al. |
| 2013/0190775 | A1 | 7/2013 | Piligian et al. |
| 2013/0297010 | A1 | 11/2013 | Bishop et al. |
| 2014/0277075 | A1 | 9/2014 | Bonnette |
| 2015/0142104 | A1 | 5/2015 | Braido |

OTHER PUBLICATIONS

Written Opinion of the International Searching Authority (PCT/ISA/237) corresponding to PCT/US16/28324 (4 pgs) dated Jul. 18, 2016.

METHOD AND APPARATUS FOR ALLOWING INFLATION OF INFLATABLE ELEMENTS WITHIN MEDICAL DEVICES

CROSS-REFERENCE TO RELATED APPLICATIONS

This U.S. utility patent application claims the benefit of priority under 35 U.S.C. § 119(e) to U.S. provisional patent application Ser. No. 62/174,252, entitled "Method And Apparatus For Allowing Inflation Of Inflatable Elements Within Medical Devices" filed on Jun. 11, 2015 and to U.S. provisional patent application Ser. No. 62/172,437, entitled "Method And Apparatus For Allowing Inflation Of Inflatable Elements Within Medical Devices" filed on Jun. 8, 2015, each of which is incorporated herein by reference in its entirety.

TECHNICAL FIELD

This disclosure is generally related to medical devices containing inflatable structures having novel connectors, such as a T junction. More specifically, the disclosure is directed to novel junctions joining an inflation lumen to an inflatable element in a medical device. The novel junctions permit fluid to pass through to inflate an inflatable element which is not co-axial with the axis of inflation. The junctions maintain a generally rigid, fixed angle in relation to the axis of the inflation lumen to create a robust structure which is resistant to deflection during use within the human body.

BACKGROUND OF THE INVENTION

Generally, inflatable medical devices are introduced into closed circulatory system vertebrates and invertebrates in their uninflated form and are inflated when they reach the site of interest. Balloon catheters are examples of inflatable devices. A balloon catheter is a type of catheter which is bendable and has an inflatable balloon at its tip. These catheters may be used to enlarge a narrow opening or passage within the body. The catheter is advanced in a subject's blood vessel so that the balloon is in the correct position. The uninflated balloon is then inflated to perform the necessary procedure, and then deflated in order to be removed from the subject's blood vessel. When balloon catheters are inflated, they can occlude the opening or passage in which they are placed. Such an occlusion is generally temporary. Occasionally, it is necessary to inflate an element of a medical device that is not co-linear with the inflation lumen connecting the inflatable element to the operator. In such an arrangement, the inflatable element is set at an angle from the axis of the supporting catheter. When inflated, for the device to function properly, a relatively rigid, fixed orientation between the catheter body and the inflatable element must be achieved and maintained. In particular, this is true of medical devices which incorporate an inflatable toroid element in order to perform a particular function. Such toroids are typically fixed perpendicularly to the supporting catheter, and must be maintained in this orientation to function properly. Other devices with inflatable elements may also require that an inflatable element be disposed at an angle with relation to the supporting catheter. In each such instance, it is crucial that a structure exists to rigidly maintain this orientation. However, such a structure has not been described in the prior art.

It would therefore be desirable for an insertable, inflatable medical device to have a stable junction point through which an inflation fluid may pass and inflate an element which is not co-linear with the axis of inflation. Accordingly, there is a need in the art for such a structure that maintains a rigid orientation between an inflatable element and a catheter body, as one does not presently exist in the art.

SUMMARY OF THE INVENTION

The present invention provides a rigid connector which joins an inflation lumen to an inflatable element in a medical device. In a preferred embodiment the inflatable element is a toroid. The connector preferably comprises a junction in which one branch of the junction connects to an inflation lumen within a supporting catheter shaft, and another branch of the junction connects to the inflatable element.

These and other features, aspects, and advantages of the present invention will become better understood with reference to the following detailed description when considered in association with the accompanying drawings and claims.

DETAILED DESCRIPTION OF THE INVENTION

Figure 1:
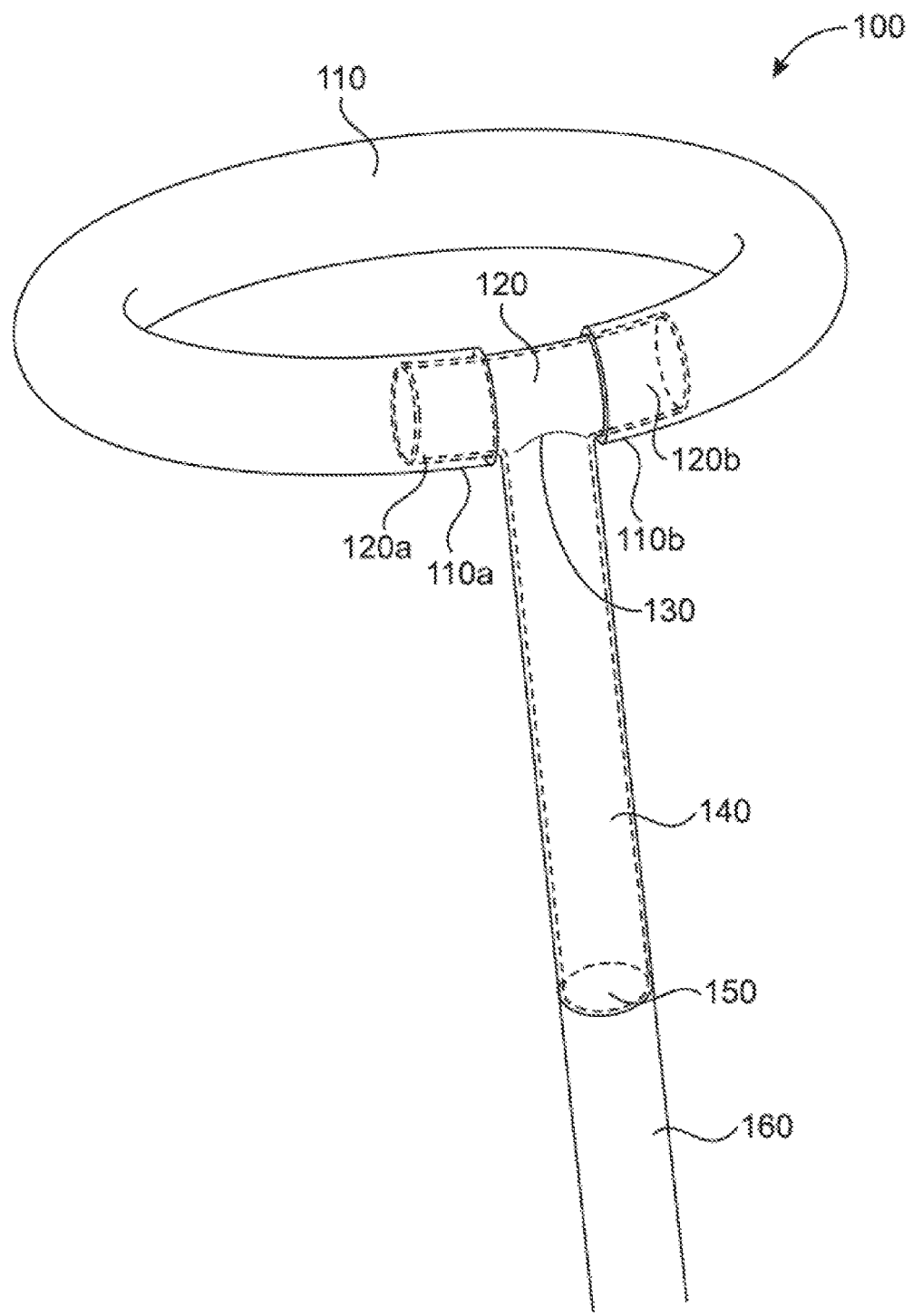
FIG. 1 shows a T junction in which the shaft is perpendicular to the crossbar of the T junction and the ends of the inflatable toroid envelop the crossbar.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Embodiments of the invention are directed to a rigid connector which joins an inflation lumen to an inflatable element in a medical device. The junction maintains a generally rigid, fixed angle in relation to the axis of the inflation lumen, which in certain embodiments is perpendicular to said axis. This is preferable in maintaining a fixed orientation between the inflatable element and the catheter shaft through which the inflation fluid is delivered. In a preferred embodiment the inflatable element is a toroid. This fixed orientation creates a robust structure which is resistant to deflection when forces are encountered during its use within tubular and non-tubular structures within closed circulatory systems.

The junctions of the present invention are rigid connectors which join an inflation lumen of a catheter to an inflatable element in a medical device. The hollow junction comprises a biocompatible material. The junction has at least one crossbar opening, continuous with at least one shaft opening. For example, the junction may have at least two openings—a first opening leading to a shaft in fluid communication with an inflation lumen of a catheter and a second opening on a crossbar and in fluid communication with an inflatable element. In one preferred embodiment the junction has three openings with a first opening leading to a shaft in fluid communication with an inflation lumen of a catheter, a second opening on a crossbar in fluid communication with a first end of an inflatable element, and a third opening on the crossbar in fluid communication with a second end of an inflatable element. In one preferred embodiment the junction has three openings and is substantially T shaped and the inflatable element is a toroid. Alternatively, there may be two separate inflatable elements, each having one opening and an opposite end that is sealed. Each opening is fluidly connected to the junction.

A preferred embodiment is a T-shaped junction where a vertical branch or shaft of the T junction connects to an inflation lumen within a supporting catheter shaft, and a crossbar of the T junction connects to the inflatable element where the shaft intersects the crossbar in a perpendicular fashion. The junction can be made in a variety of shapes such as a "T", a "Y", or an "L". In one embodiment the T junction has a crossbar and the crossbar is perpendicular to and in the same plane as the shaft. Alternatively, the crossbar may be perpendicular to the shaft but extended in a second plane from the shaft. While the preferred embodiment is in a "T" configuration, other embodiments, in which the fixed orientation of the inflatable element is other than perpendicular, are also disclosed. The junction may have two, three, four, five, six, seven, eight, nine, ten, eleven, or twelve openings or more than twelve openings. In another preferred embodiment the junction has three or more openings. In an alternative embodiment, no further support structure beyond the rigid bar of the T junction is needed to create a rigid structure that is perpendicular to the shaft. The T junction of the present invention is useful in a variety of catheter-based medical devices, such as embolectomy catheters, inflatable intraluminal stents, snare catheters, detachable devices including stents or stent-grafts, aortic stent grafts, inflatable cardiac valves, and inflatable inferior vena cava filters.

The junction is composed of any biocompatible material that is generally rigid at its point of angulation. Preferred materials include, but are not limited to, metals, polymers, and ceramics. Non-limiting examples of materials that the junction may be made of include titanium, aluminum, copper, nickel, platinum, silver, tantalum, tungsten, steel, nitinol, or alloys thereof. In one preferred embodiment the junction is titanium; in one preferred embodiment the junction is tantalum; in one preferred embodiment the junction is tungsten. Additional non-limiting examples of junction materials include a rigid polymer such as, polyethylene (PE), polyethylene terephthalate (PET), polypropylene (PP), polytetrafluoroethylene (PTFE), polycarbonate (PC), polyacrylate, polyvinyl chloride (PVC), polyamide, polyether block amide (PEBA), acrylonitrile butadiene styrene (ABS), or blends or mixtures thereof. The junction may be made of, but not limited to, ceramics including bioceramics, porcelain type ceramics, piezoceramics, glass ceramics.

The junction is preferably formed of a single material but may be comprised of two or more materials (such as a T junction having a first material for the shaft and a second material for the crossbar). In one embodiment the entire T junction is made of titanium; in another embodiment the crossbar of the T junction is made of polypropylene and the vertical branch of the T junction is made of 316 stainless steel.

In one embodiment the junction may have subcomponents which are flexible, and composed of a material including but not limited to, metallic, plastic, ceramic, or other materials. Subcomponents may be constructed to have varying degrees of flexibility along their lengths by, for example, altering the material utilized, altering the thickness of material, altering the processing of material, and a combination of these alterations.

Another embodiment is directed to an inflatable element which is attached to the junction at the crossbar. The inflatable member is coupled to the crossbar in a concentric fashion. In a preferred embodiment the inflatable element is toroidal; in a preferred embodiment the toroidal inflatable element is attached to a T junction. Any of a variety of cross sectional shapes may be employed in the inflatable element including a circle, oval, or other polygonal shapes including rectilinear. In a preferred embodiment when the toroid is inflated it is in a plane that is perpendicular to the shaft. In this embodiment, the crossbar of the T junction is hollow, and each end of the toroid is connected to corresponding ends of the crossbar. Supplying a fluid to the inflatable toroid through the inflation lumen and the T junction inflates the toroid. When the fluid is removed, the toroid is deflated. The inflatable element may have a variety of useful shapes including a single lobe, a toroid, a double toroid (e.g., a figure eight), a double overlapping toroid, a triple-lobe toroid, or a curved Y-shaped toroid.

In a preferred embodiment non-limiting examples of the inflatable element material include polyethylene terephthalate, nylon, polyethylene, polyurethane, polyvinyl chloride, and expanded polytetrafluoroethylene.

The direction of inflation of the inflatable element may be chosen from between 180 degrees to the catheter shaft (directly upwards) to nearly 0 degrees (nearly directly down). In a preferred embodiment the direction of inflation is perpendicular (90 degrees) to the direction of the catheter shaft. In another preferred embodiment the direction of inflation is 135 degrees to the catheter shaft. The direction of inflation to the direction of the shaft may be at or about 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 95 degrees, 100 degrees, 105 degrees, 110 degrees, 115 degrees, 120 degrees, 125 degrees, 130 degrees, 135 degrees, 140 degrees, 145 degrees, 150 degrees, 155 degrees, 160 degrees, 165 degrees, 170 degrees, 175 degrees, or 180 degrees. In a preferred embodiment having a T junction and a toroid, the plane of the toroid is preferably oriented perpendicular to the plane of the shaft. In one embodiment the plane of the toroid is oriented at less than 90 degrees and greater than 0 degrees relative to the shaft; in one embodiment the plane of the toroid is oriented at more than 90 degrees and less than or equal to 180 degrees relative to the shaft.

In a preferred toroidal inflatable element embodiment the T junction intersects the toroidal member on the planar sides (like a ladle handle intersecting the scoop), the outer perimeter (like a tennis racket handle intersecting a racket head), or the inside (like spokes intersecting a bicycle tire).

The preferred toroidal configuration may be used in many of the same procedures in which a traditional balloon catheter may be used. For example, a toroidal catheter may be used in place of a balloon catheter in angioplasty. The toroidal catheter, in an uninflated arrangement, is positioned at the proper site in a vessel. The toroid is then inflated so the toroid engages the interior wall of the vessel; inflation may cause enlargement of the vessel in which it is placed to ensure a snug fit within the vessel. The catheter is then deflated and withdrawn. Preferably the inflatable toroid may be inflated to at least 8 atmospheres; preferably the toroid is inflated to about 8 atmospheres. When a standard balloon catheter is inflated in a vessel such a blood vessel, it entirely occludes the vessel in which it is placed. However, the toroidal catheter has a central opening when it is inflated and thus it does not completely occlude a vessel when inflated. This structure allows the catheter for use in vessels which should not be occluded, for example blood vessels going to the brain.

The inflation medium is a fluid and may be either a liquid or gas. Preferred liquids include saline, water, and polymers such as polyethylene glycol or solidifyable polymers (optionally including curing and hardening agents). Contrast agents may be included with the inflation fluid to assist with positioning of the inflatable toroid. While in most instances liquid is the preferred inflation fluid, gas, such as nitrogen, helium, argon, $CO_2$ or air may also be used. Gas may be used as an inflation medium in instances where a lower pressure is required for inflation or where supercooled temperatures may be beneficial.

Various additional and optional components may be coupled to the inflatable element. In an embodiment where the inflatable element is a toroid, the inflatable toroid may be coupled to a membrane, for example, a non-porous membrane for collecting material such as emboli or a porous membrane for permitting passage of fluids therethrough. In one embodiment the membrane is liquid impermeable; in another embodiment the membrane is liquid permeable. In one embodiment the membrane may form a funnel shape tapering away from a supporting catheter; in another embodiment the membrane may form a funnel shape tapering toward a supporting catheter. As the toroid is inflated in a subject's vessel, the membrane is deployed within the vessel—for example forming a net. In an embodiment where the inflatable element is a toroid, the inflatable toroid may be attached to a wire or filament running through a lumen of the catheter; the inflatable toroid may be attached to one or more than one rigid support arm or other projection extending from an end of a supporting catheter. Such projections may be engaged for additional toroid support, to assist with placement of the device within a vessel, and/or to permit (or restrict) movement of the toroid during use. Radiopaque markers may be affixed to the inflatable element to assist with radiographic imaging when positioning a device of the embodiments of the invention within a vessel.

In one embodiment a filament is used to assist with deflation and collapse of the inflatable toroid. In one embodiment a filament runs through the inside of the inflatable toroid and T junction and can be retracted to close the toroid like a lasso. In one preferred embodiment the inflatable toroid is coupled to a membrane in a net-like fashion; in another embodiment the inflatable toroid is coupled to a filament to permit collection and capture of an object within the interior of the net of the membrane.

Membranes useful in the inventive medical devices described herein may be porous or non-porous. The degree of porosity can be selected depending on the particular medical device and application. Preferred membranes are formed of flexible materials; preferred polymeric and elastomeric materials include polyurethane (available from AdvanSource biomaterials as CHRONOTHANE®), latex, polyethylene terephthalate, nylon, polyethylene, polyvinyl chloride, and expanded polytetrafluoroethylene. Alternatives to porous membranes useful in the invention include netting, webbing, filaments, and mesh so that porosity can be controlled. Such materials may include knit or woven textiles.

A goal of the present invention is to provide a medical device that is inserted into a subject in a first low-profile configuration and then inflated to a second larger configuration in a subject's vessel during a medical procedure. In one preferred embodiment the inflated device may subsequently be deflated to a third low-profile configuration so the device can be removed from the patient or relocated within a vessel; in another preferred embodiment the inflated device is detached from the delivery catheter and remains implanted in the subject in its second larger and inflated state. It is preferred that the inventive medical devices are capable of multiple inflation and deflation cycles; preferred embodiments are used in single deployment environments.

FIG. 1 shows a preferred embodiment 100 of the T junction in which the shaft 140 is perpendicular to the crossbar 120 and the ends of the inflatable toroid (110a and 110b) envelop the crossbar 120. As detailed in FIG. 1, a toroid 110 is attached to corresponding ends (120a and 120b) of the crossbar 120 of the T junction. The ends of the toroid (110a and 110b) envelop the ends of the crossbar 120 (120a and 120b respectively) and may be bonded with adhesive or by curing, melting, by using friction or any other suitable methods. The crossbar 120 surface may be treated in a manner to enhance the bonding, for example, with a roughened surface or grooves, or by tapering or barbing the ends. The crossbar 120 may also have a taper or other shape modification to enhance bonding or fabrication methods. The crossbar 120 is joined at junction 130 to shaft 140. The fusion point of the junction 130 may be of a single piece or represent the welding or bonding of crossbar 120 to shaft 140. A continuous lumen 150 extends through the junction, that is from the end of shaft 140 furthest from the crossbar and throughout the hollow members of both the shaft 140 and the crossbar 120. The continuous lumen 150 is in fluid communication with an inflation lumen 160 within a support catheter (not shown). The inflation lumen 160 is connected to shaft 140 and may optionally be connected through a valve. Shaft 140 may be permanently fixed to inflation lumen 160 or may be selectively detachable from inflation lumen 160. It will be advantageous to utilize an embodiment where shaft 140 is fixed to inflation lumen 160 in instances where the medical device is intended to be deployed within a vessel then deflated and removed from the vessel. It will be advantageous to utilize an embodiment where shaft 140 is selectively detachable from inflation lumen 160 in instances where the medical device is intended to be deployed and reside within a vessel in an inflated state for long-term or permanent placement. The shaft 140, crossbar 120, and inflatable element 110 share a common lumen and are all fluidly connected.

A guidewire is typically used in operating a device incorporating the invention but a guidewire is not required. In instances where a guidewire is utilized, a separate guidewire lumen is associated with the device.

Figure 2:
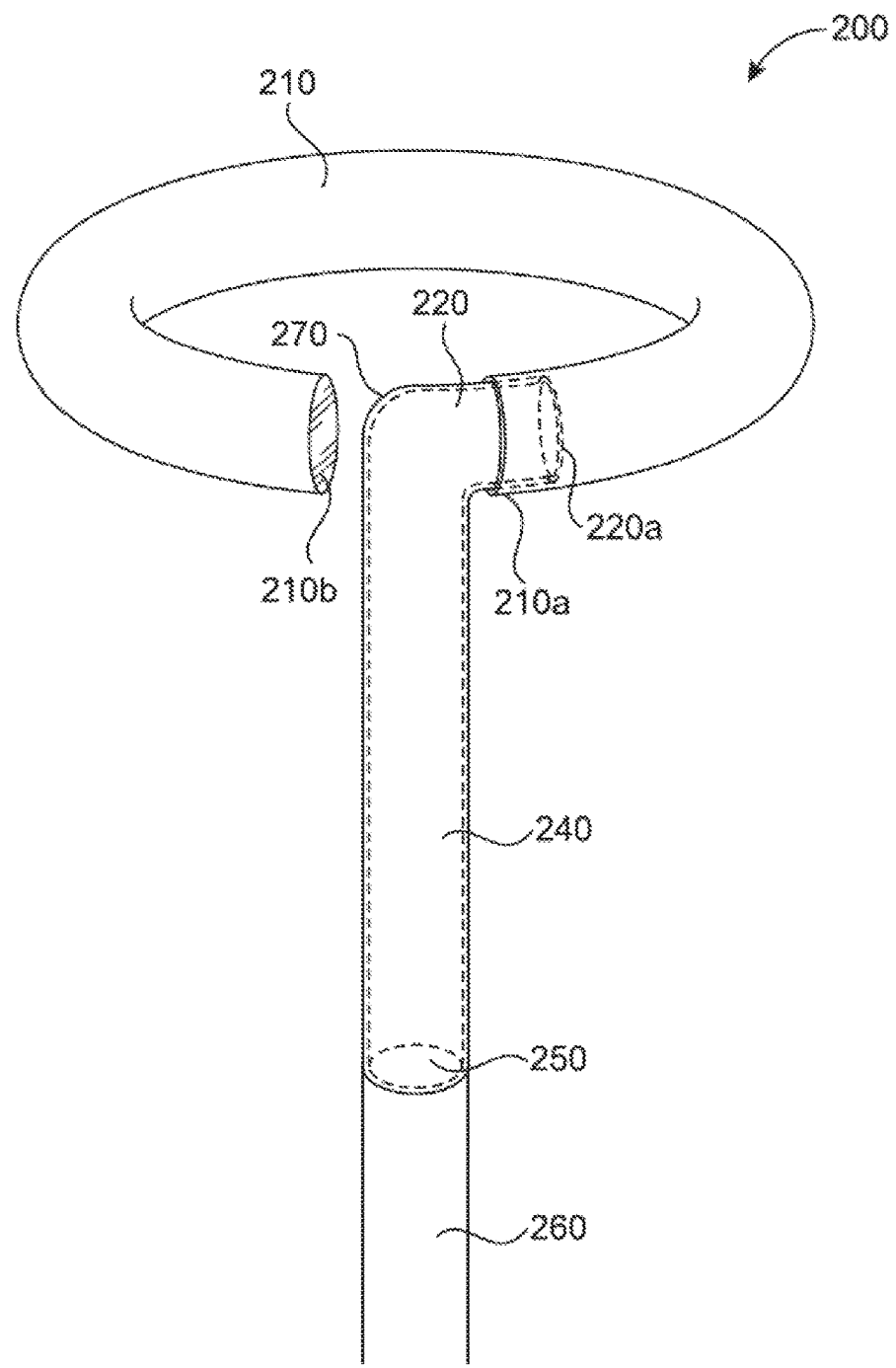
FIG. 2 shows a T junction in which one of the two ends of the crossbar of the T junction of FIG. 1 is sealed. The inflatable toroid is also sealed at one end, so the toroid inflation takes place unilaterally through the open end of the crossbar.

FIG. 2 shows an alternative embodiment 200 of the rigid connector, in an "L" configuration. In this embodiment, toroid 210 has a single open end 210*a* attached to single crossbar 220 at open end 220*a*. The other end of the toroid is sealed at 210*b* (blind pouch). This embodiment allows for a more simplified fabrication process while maintaining the necessary rigidly imposed angulation at 270 of the junction; a toroid 210 that is attached to a single open end 220*a* of crossbar 220 requires a seal at only one location as opposed to two locations, as depicted in FIG. 1. In this embodiment, angulation 270 of the junction is at 90 degrees in the same plane as the shaft 240, although angulation 270 may also be at angles other than 90 degrees. The toroid 210 is then inflated through the inflation lumen 260, which conducts fluid through the junction lumen 250 continuously through shaft 240 to crossbar 220 and into toroid 210. As in FIG. 1, the bonding of inflation lumen 260 to shaft 240 may be accomplished through a variety of processes, including adhesives, curing, melting, or a valvular or frictional arrangement.

Figure 3:
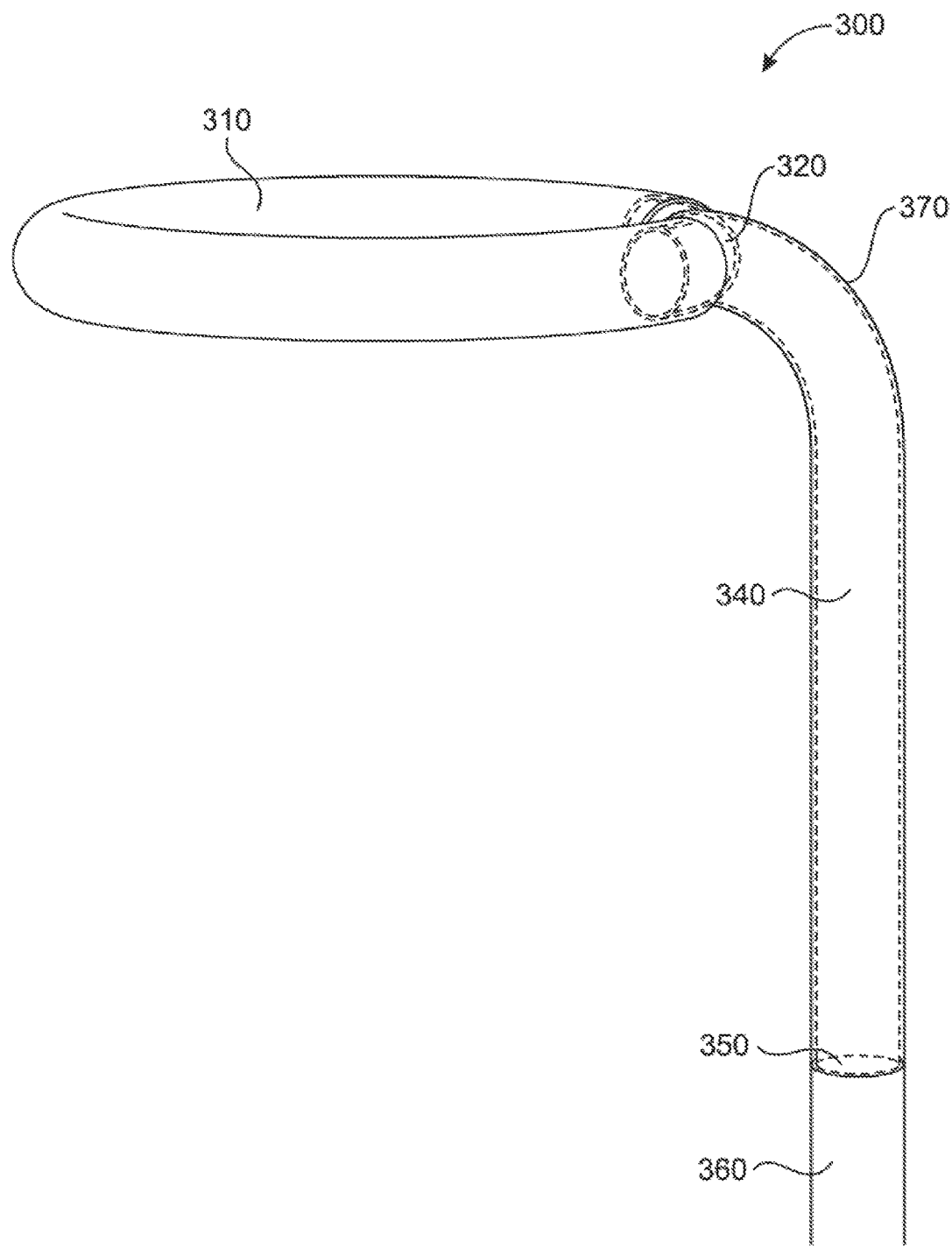
FIG. 3 shows an embodiment of the T junction, in which the shaft of the T junction has an angulation within it. This allows the inflatable element, which in FIG. 3 is a toroid, to be fixed in a different plane from that of the shaft of the T junction.

FIG. 3 shows a sideview of another preferred embodiment 300 of the rigid connector, in which the shaft of the connector has a shape other than linear. In this configuration, the hollow shaft 340 with lumen 350 extends throughout the hollow junction to its crossbar 320 seen end-on. The modification compared to the embodiment in FIG. 1 is the addition of an angulation 370 in shaft 340 into the plane of the toroid 310, such that crossbar 320 is no longer in the same plane as shaft 340. This allows the toroid 310, attached to crossbar 320 in similar fashion with other embodiments, to be elevated away from the wall of a tubular structure into which the device is introduced. The toroid is inflated and deflated through inflation lumen 360, in fluid communication with lumen 350 of shaft 340. This allows the inflatable element 310 to be thus displaced in a fashion that it may be centered within a tubular structure (e.g., blood vessel) with the body. This configuration gives the rigid connector and toroid combination directionality—rotating the shaft 340 of the catheter permits rotation of the toroid to various areas of a lumen within a closed circulatory system, particularly if the toroid is significantly smaller than the lumen (vessel or tubular structure) in which the toroid is deployed. This may be particularly useful in snare catheter embodiments.

Figure 4:
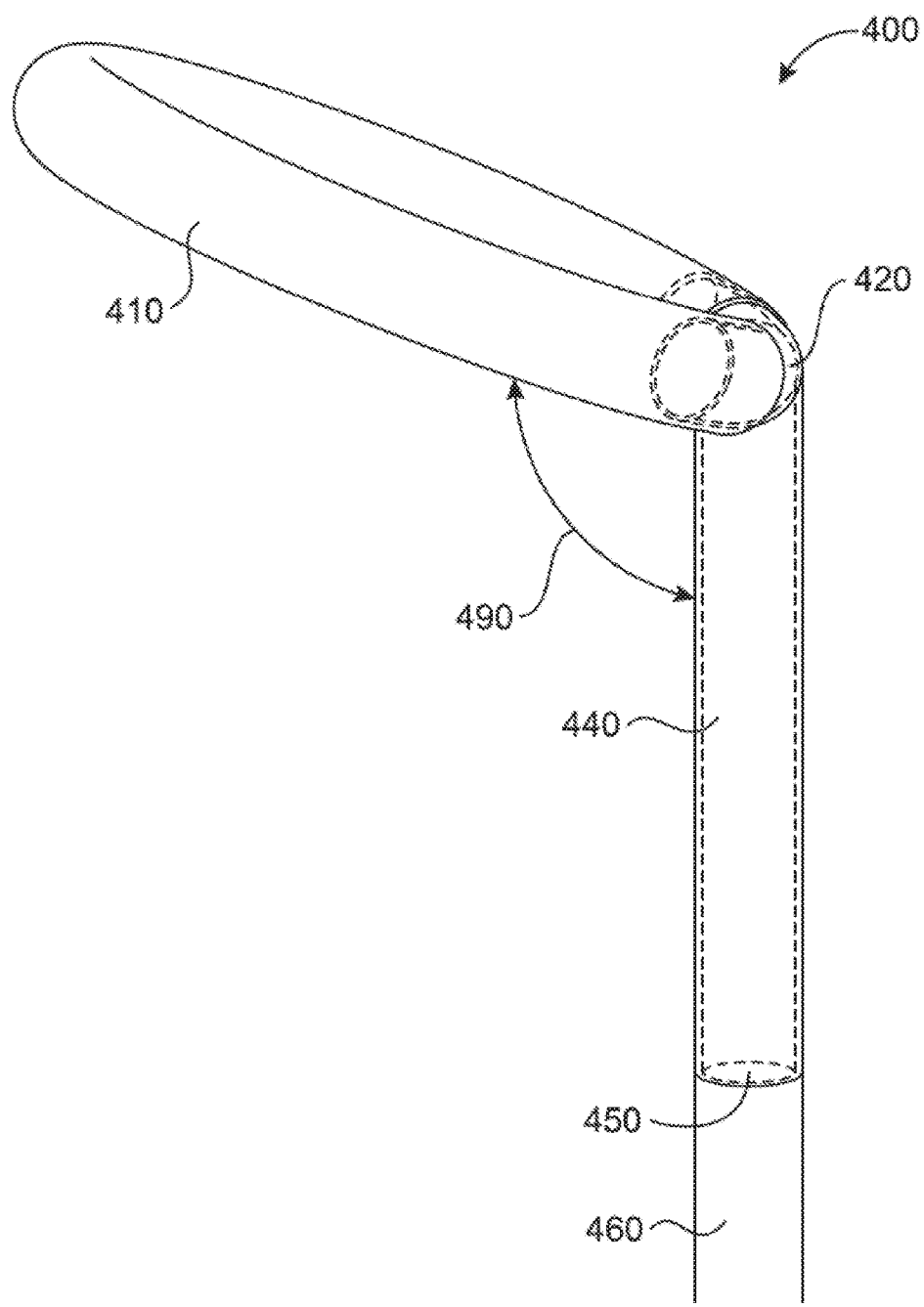
FIG. 4 shows an embodiment of the T junction in which the toroidal attachment is affixed at an angle other than perpendicular to the shaft.

FIG. 4 shows a sideview of another embodiment 400 of the invention, in which the inflatable toroid is attached to a T junction at an angle of about 120 degrees measured between the plane of the inflatable element 410 and the direction of shaft 440, as shown at angle 490. In this configuration, the inflatable toroid 410 is attached to the ends of crossbar 420 by any of a variety of bonding techniques as previously described for FIG. 1. Said bonding, in this configuration, is carried out in such a fashion that the toroid 410 is disposed at an oblique angle 490 relative to the shaft 440 of the T junction. The toroid 410 is inflated using inflation lumen 460 through the hollow member of the T junction connector comprising shaft 440 and crossbar 420 through lumen 450. There are numerous situations in which such a configuration would be advantageous in a clinical setting, as the oblique disposition of the toroid 410 generates different forces on the surrounding structures in an oblique orientation, relative to those forces generated in a right-angle configuration.

Figure 5:
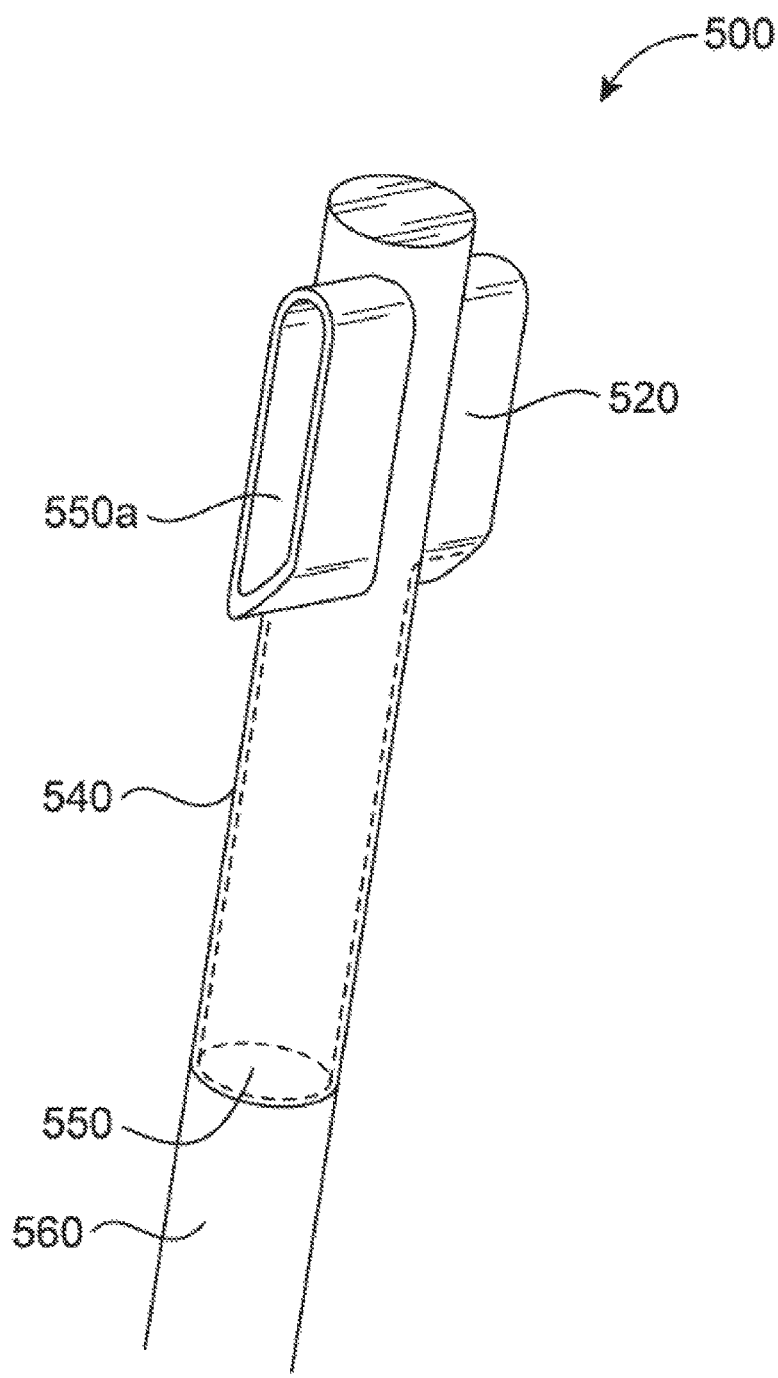
FIG. 5 shows an embodiment of the device in which the cross-section of the T junction is non-circular.

FIG. 5 shows a perspective view of an alternative embodiment 500 of the current invention. In this configuration the shaft 540 of the T junction connector is joined to a crossbar 520 with a lumen 550*a* having a cross section that is non-circular. The non-circular lumen 550 may be elliptical, ovoid, tear-shaped, rectangular, square or any other conceivable and useful shape and may have beveled or rounded edges. The non-circular lumen 550 allows improved engagement with inflatable elements which do not have circular cross-sections. The inflatable element is inflated through inflation lumen 560 via lumen 550 of the shaft 540 of the T junction connector, which is in fluid communication with the non-circular lumen 550*a* of crossbar 520. For crossbars having lumens which do not have circular cross-sections, the long axis of the cross section may be oriented lengthwise with the shaft (such as if a toroid is a tall cylinder) or may be perpendicular to the shaft (such as if a toroid is a flattened donut).

Figure 6A:
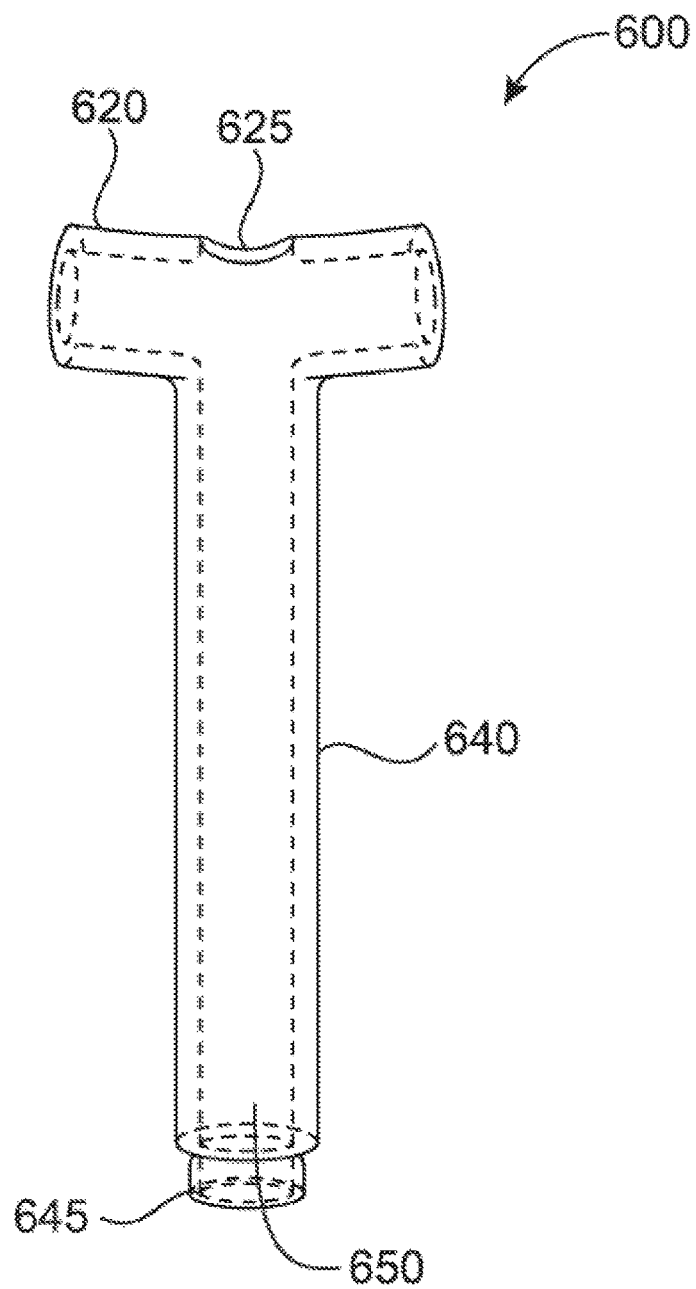
FIG. 6A shows an embodiment of a modular T junction.

FIG. 6A shows another embodiment of the invention in a frontal view. This embodiment discloses a modular connector which can be combined with additional connectors as demonstrated in FIG. 6B. In FIG. 6A, the shaft 640 of the connector is joined to crossbar 620 as previously described. The current embodiment is modified in that there is an orifice 625 at the midpoint of the crossbar 620 which creates a fluid communication through lumen 650 with crossbar 620 and shaft 640. In addition to this modification, the distal end of the shaft 640 is configured to create a junction point 645 on a first module connector which can actively engage or be bonded to orifice 625 on a second module connector when multiple connectors are combined, as seen in FIG. 6B.

Figure 6B:
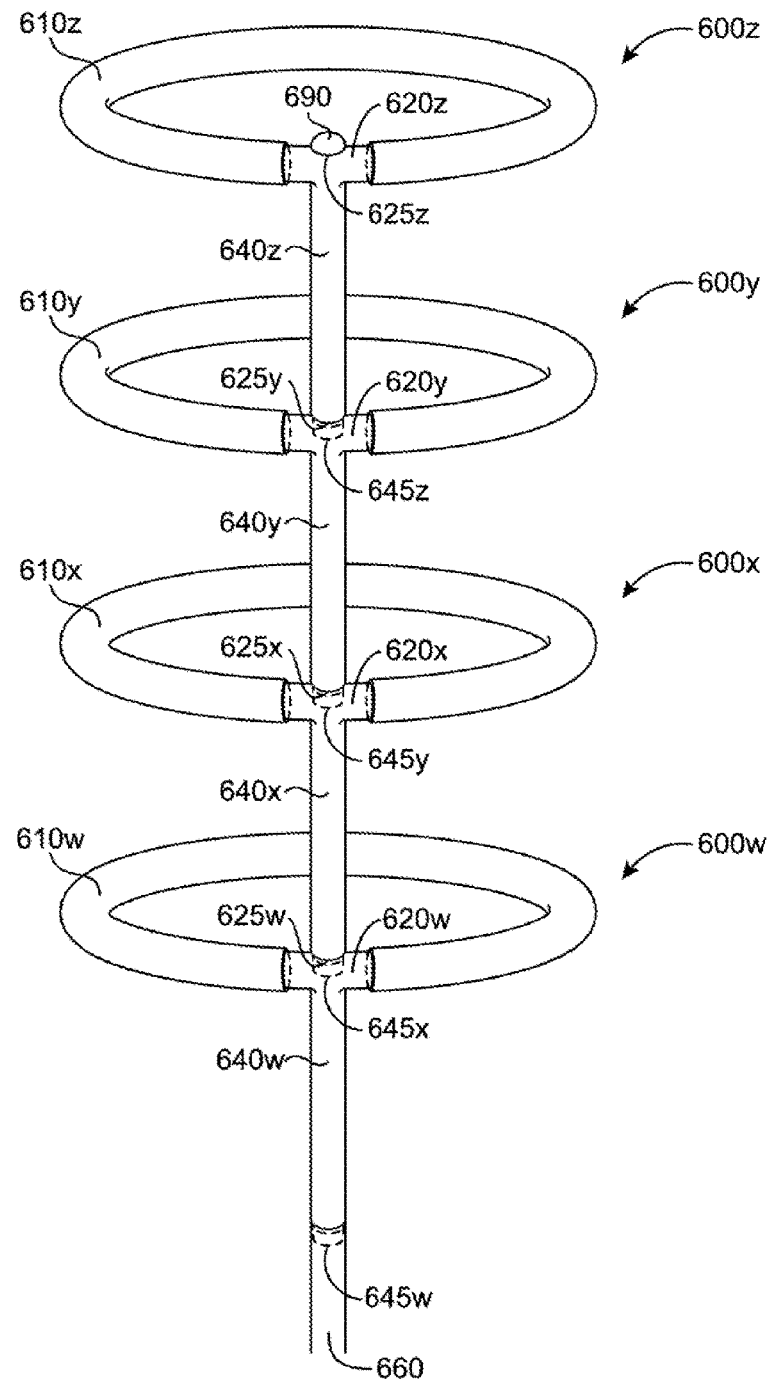
FIG. 6B shows an embodiment in which a series of modular T junction/toroidal complexes are joined to form an inflatable stent.

FIG. 6B shows an example of a possible combination of the connectors outlined in FIG. 6A. The device of FIG. 6B is comprised of four repeating modules (600*z*, 600*y*, 600*x*, and 600*w*) each having its own inflatable toroid (610*z*, 610*y*, 610*x*, and 610*w*), crossbar (620*z*, 620*y*, 620*x*, and 620*w*), shaft (640*z*, 640*y*, 640*x*, and 640*w*), orifice (625*z*, 625*y*, 625*x*, 625*w*) and the four modules meet at three junction points (645*z*, 645*y*, 645*x*), where two modules are connected through a single junction point. Module 600*z* is connected to adjacent module 600*y* at junction point 645*z* where modified shaft 640*z* and orifice 625*y* of FIG. 6A are engaged. Each module's crossbar (620*z*, 620*y*, 620*x*, and 620*w*) is bonded to its own inflatable toroid (610*z*, 610*y*, 610*x*, and 610*w*), and the combined assembly creates a "spine" of shafts (640*z*, 640*y*, 640*x*, and 640*w*) with toroids (610*z*, 610*y*, 610*x*, and 610*w*) forming an inflated segmented cylinder. Such a configuration is useful as a conduit or stent. The end 645*w* is joined to inflation lumen 660 either by bonding or a configuration which allows the inflation lumen 660 to be detached. In one embodiment the system may be sealed by a valve or plug between end 645*w* and catheter lumen 660. To maintain a closed system for inflation, the distal most module 600*z* has plug 690 seal the distal orifice 625*z*.

Figure 7:
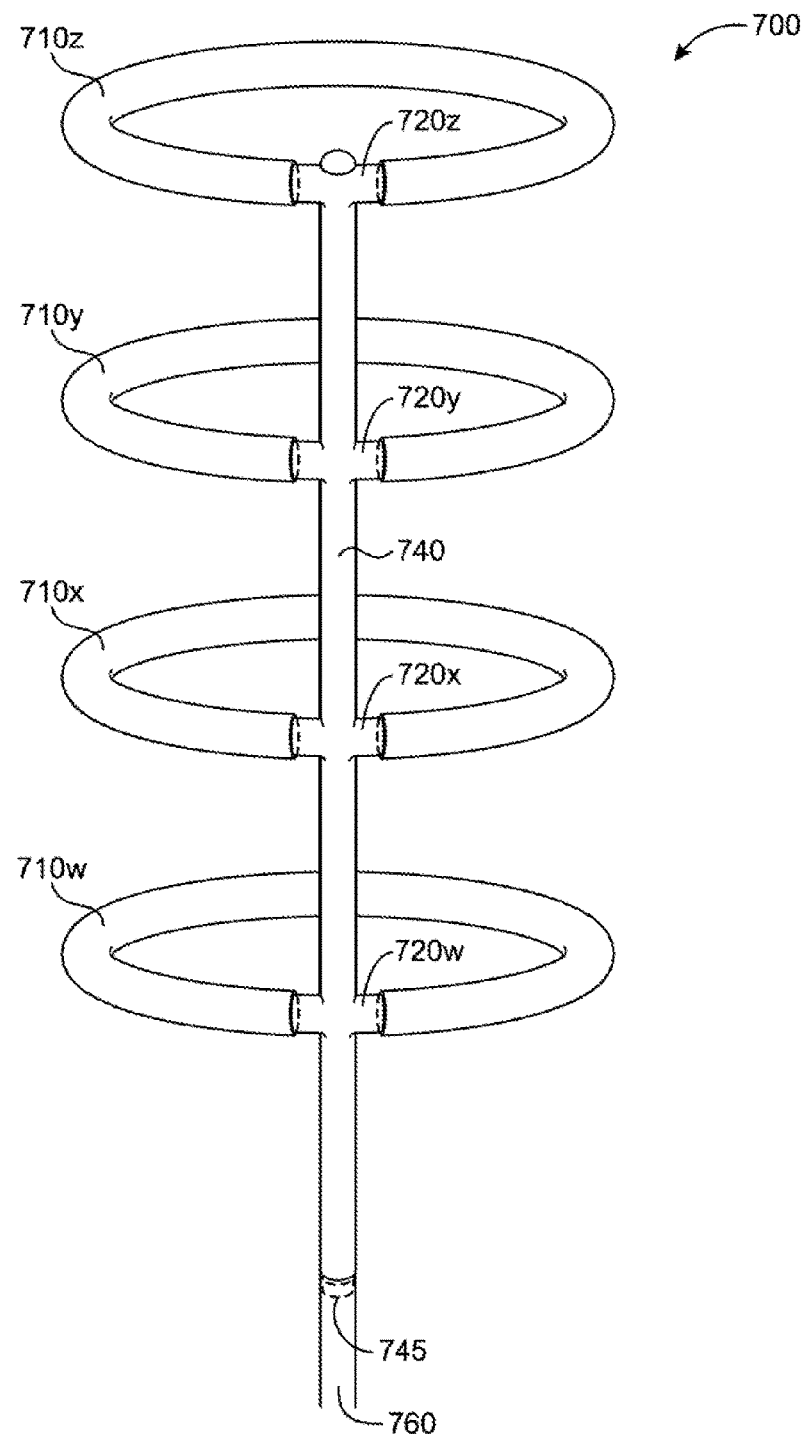
FIG. 7 shows an embodiment with a single shaft with a multi-crossbar connector.

FIG. 7 shows a multi-crossbar connector in frontal view. Rather than the modular combination demonstrated in FIG. 6B, this configuration 700 combines as a single unit the multiple modules. The shaft 740 incorporates multiple crossbars (720*z*, 720*y*, 720*x*, and 720*w*), each of which is attached to inflatable toroids (710*z*, 710*y*, 710*x*, and 710*w*). Modified end 745 is connected to inflation lumen 760, which is in fluid communication with the lumen of shaft 740, crossbars (720*z*, 720*y*, 720*x*, and 720*w*), and toroids (710*z*, 710*y*, 710*x*, and 710*w*).

Figure 8:
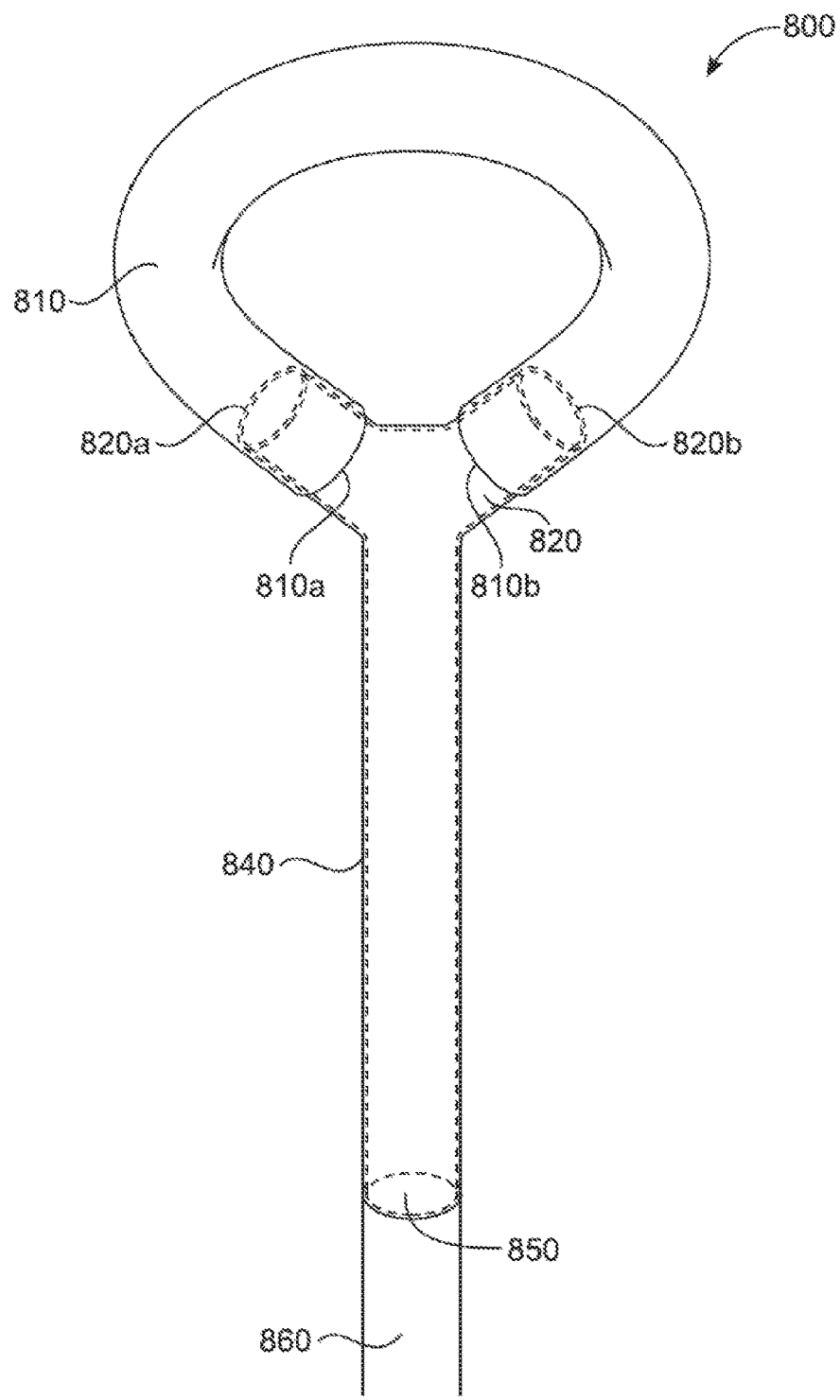
FIG. 8 shows an embodiment in which the crossbar of the connector is not perpendicular to the shaft of the connector (Y junction) and is in the same plane as the shaft.

FIG. 8 shows an alternative embodiment 800 of the invention in which the crossbar 820 of a Y junction connector is in an orientation not perpendicular to the shaft 840 and in the same plane as the shaft. Shaft 840 is connected to crossbar 820 whose ends (820*a* and 820*b*) in turn are bonded to ends 810*a* and 810*b* of toroid 810. Such a configuration disposes the toroid 810 in an orientation not perpendicular to the axis of the shaft 840, which can be advantageous in catheters that have snaring functions. Toroid 810 is in the same plane as the direction of shaft 840 and is fluidly connected via crossbar 820 and shaft 840 of the connector via lumen 850 and inflatable lumen 860.

Figure 9:
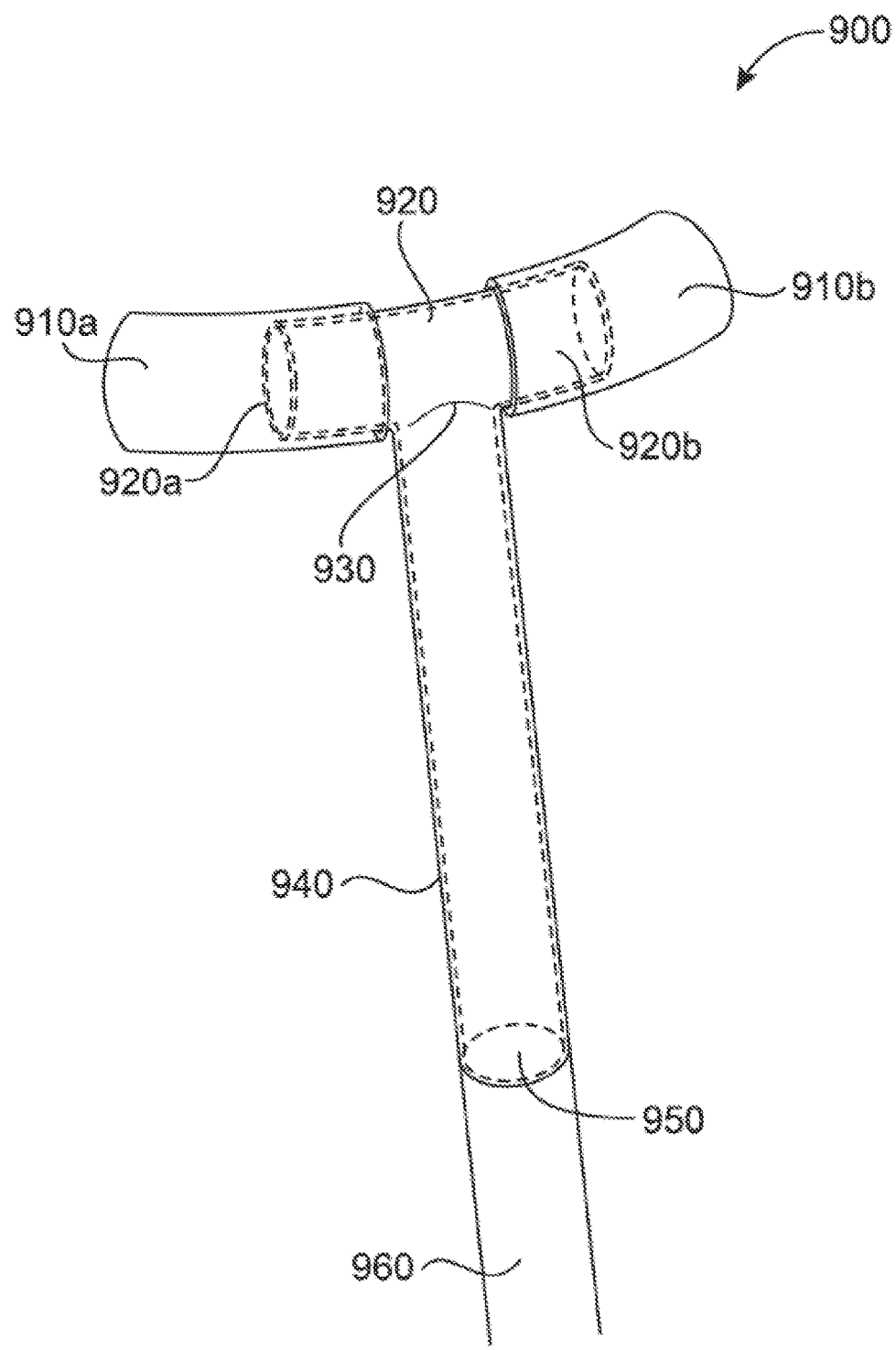
FIG. 9 shows an alternative embodiment having two non-toroidal inflatable elements, one inflatable element attached to each end of the crossbar.

FIG. 9 shows an alternative embodiment 900 of the invention in which the inflatable element attached to the connector is non-toroidal. The shaft 940 of the connector joins at junction point 930 with the crossbar 920 as similarly outlined in FIG. 1. Linear inflatable elements 910*a* and 910*b* are bonded to crossbar 920 ends 920*a* and 920*b* either through the use of adhesives, melting, curing, or mechanical means such as a friction fit or suture binding. Linear inflatable elements 910*a* and 910*b* are inflated via inflation fluid which is conducted through lumen 950 and inflation lumen 960. Such a construction may be used in a catheter-based system in which the linear inflatable elements are used to agitate a semi-solid or solid material in a bodily cavity or tubular structure in order to fragment it for easier removal. Alternatively, such a configuration may be used to anchor a catheter within a bodily structure. Non-toroidal inflatable elements may include but are not limited to linear, spiral, corkscrew, spherical or other shapes. One or more non-toroidal inflatable elements may be used, for example two linear inflatable elements shown in FIG. 9, three inflatable elements in a triangular configuration, four elements in an X-shaped configuration, or more than four elements.

Figure 10:
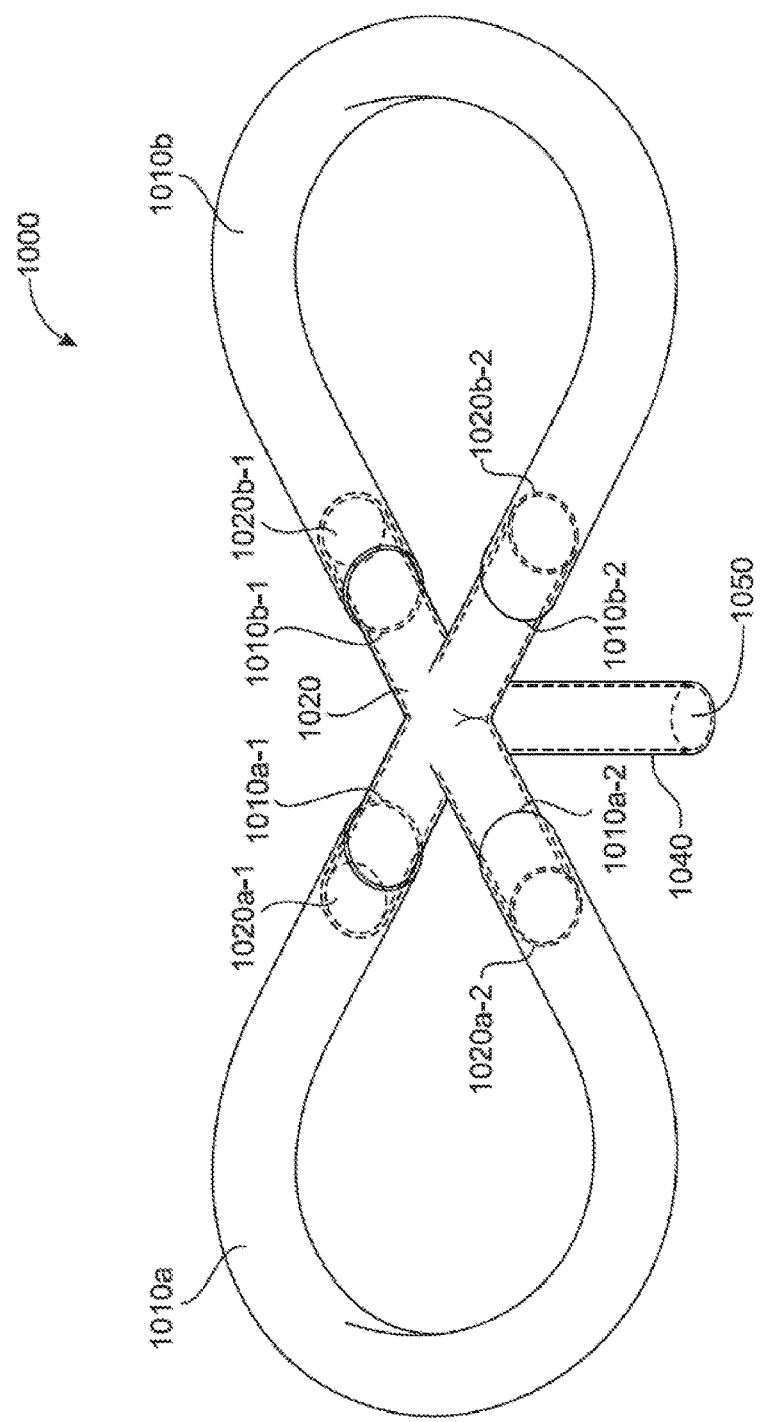
FIG. 10 shows an X junction in which the shaft is perpendicular to the plane of the crossbars of the X junction and two inflatable toroids are oriented in a "figure eight" manner in the plane of the crossbar.

FIG. 10 shows an alternative embodiment 1000 of the rigid connector, in an "X" configuration having four ports to the inflatable elements 1010*a* and 1010*b*. Shaft 1040 is perpendicular and fluidly connected to the "X" crossbar 1020. Two inflatable toroids 1010*a* and 1010*b* are oriented in a "figure eight" manner in the plane of the crossbar 1020. In this embodiment, a first toroid 1010*a* has open ends 1010*a*-1 and 1010*a*-2 attached to two adjacent ends of crossbar 1020 at ends 1020*a*-1 and 1020*a*-2; a second toroid 1010*b* has open ends 1010*b*-1 and 1010*b*-2 attached to two adjacent ends of crossbar 1020 at ends 1020*b*-1 and 1020*b*-2. The toroids 1010*a* and 1010*b* are inflated through lumen 1050 of shaft 1040.

Figure 11:
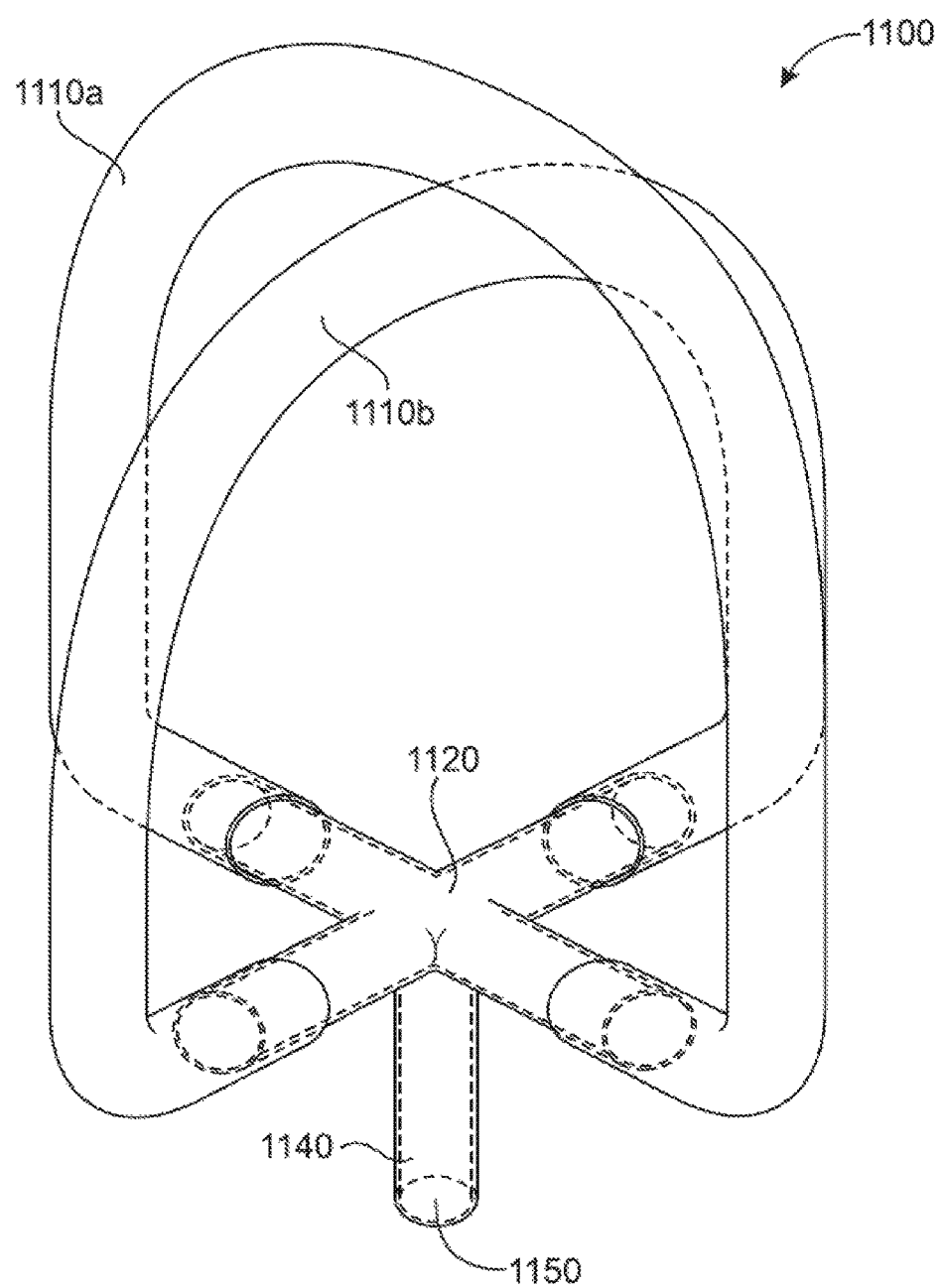
FIG. 11 shows an X junction in which the shaft is perpendicular to the plane of the crossbars of the X junction and two inflatable toroids are oriented out of the plane of the crossbar in the direction of the shaft.

FIG. 11 shows an alternative embodiment 1100 of the rigid connector, in an "X" configuration having four ports to the inflatable elements 1110*a* and 1110*b*. Shaft 1140 is perpendicular and fluidly connected to the "X" crossbar 1120. Two inflatable toroids 1110*a* and 1110*b* are oriented out of the plane of the crossbar 1120 and in the direction of the shaft 1140. The toroids 1010*a* and 1010*b* are inflated through lumen 1050 of shaft 1040.

Figure 12:
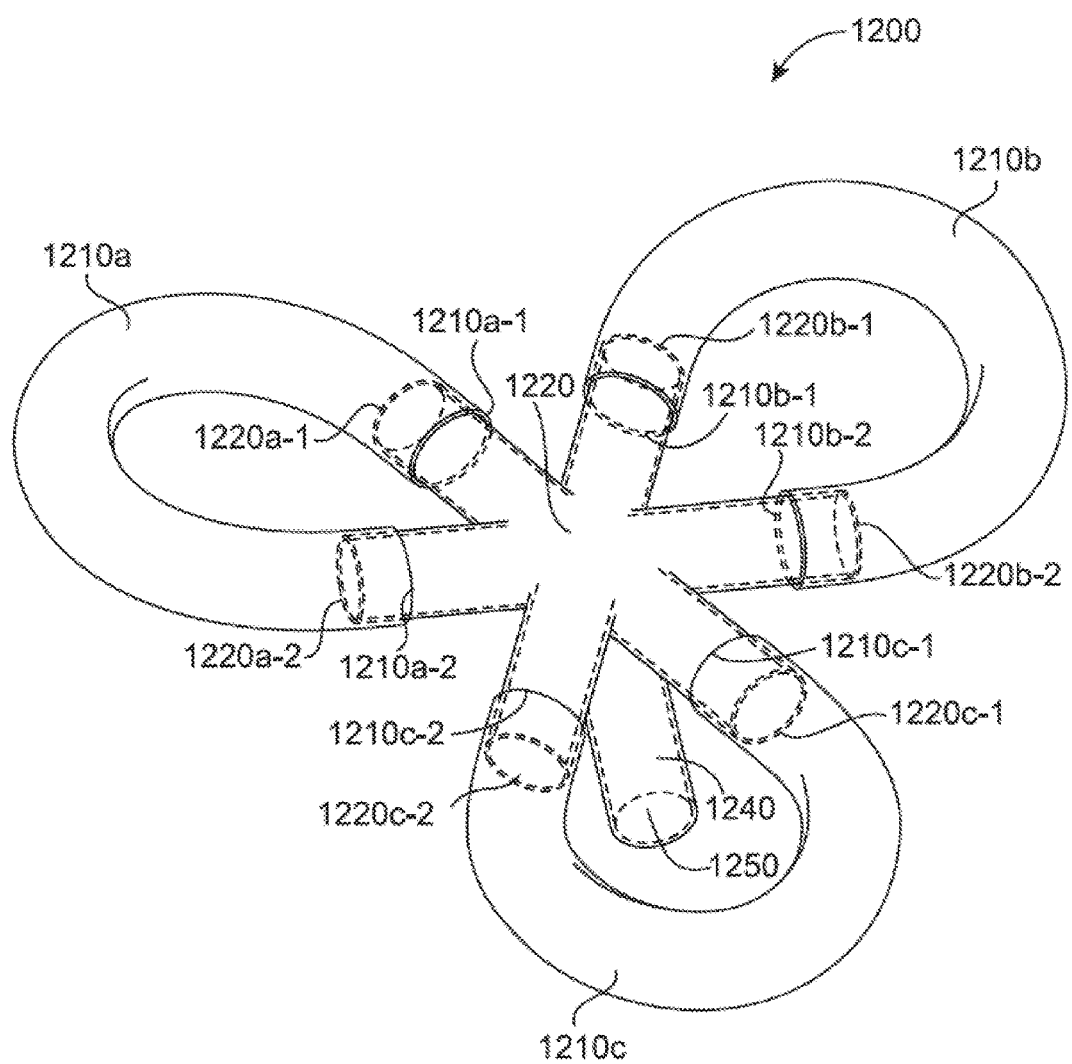
FIG. 12 shows a 6-port junction in which the shaft is perpendicular to the plane of the crossbar of the 6-port junction and three inflatable toroids are oriented in the plane of the crossbar.

FIG. 12 shows an alternative embodiment 1200 of the rigid connector, in a 6-port configuration to the inflatable elements 1210*a*, 1210*b*, and 1210*c*. FIG. 12 shows a 6-port crossbar 1220 in which the direction of shaft 1240 is perpendicular to the plane of the crossbar of the 6-port configuration and three inflatable toroids are oriented in the same plane as the crossbar. Shaft 1240 is perpendicular to the 6-port crossbar 1220. Three inflatable toroids 1210*a*, 1210*b*, and 1210*c* are each oriented in the plane of the crossbar 1220. In this embodiment, a first toroid 1210*a* has open ends 1210*a*-1 and 1110*a*-2 attached to crossbar 1220 at two adjacent ends 1220*a*-1 and 1220*a*-2; a second toroid 1210*b* has open ends 1210*b*-1 and 1210*b*-2 attached to crossbar 1220 at two adjacent ends 1220*b*-1 and 1220*b*-2; and a third toroid 1210*c* has open ends 1210*c*-1 and 1210*c*-2 attached to crossbar 1220 at two adjacent ends 1220*c*-1 and 1220*c*-2. The toroids 1210*a*, 1210*b*, and 1210*c* are inflated through lumen 1250 of shaft 1240.

Figure 13:
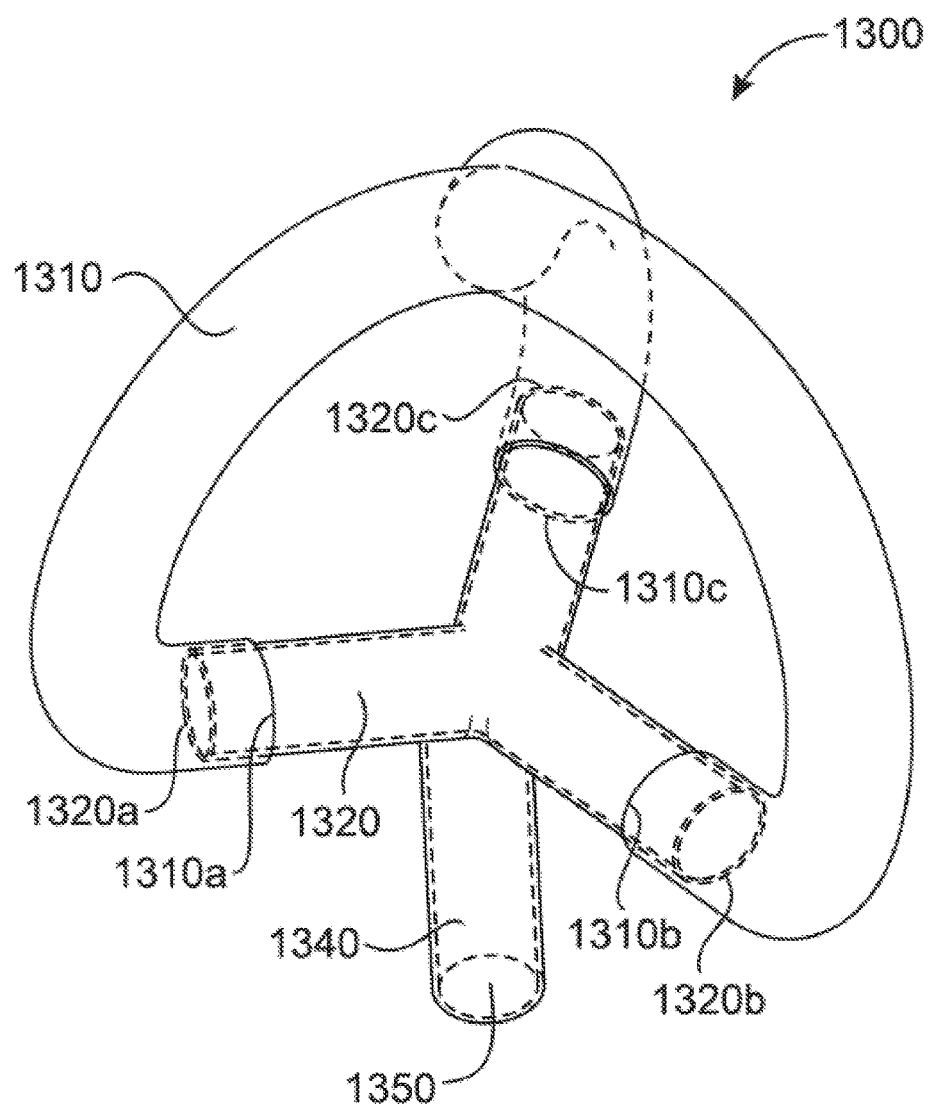
FIG. 13 shows a tri-port junction in which the shaft is perpendicular to the plane of the crossbar of the tri-port junction and an inflatable Y-shaped-curved element is oriented out of the plane of the crossbar generally in direction of the shaft.

FIG. 13 shows an alternative embodiment 1300 of the rigid connector, in a tri-port configuration to the inflatable element 1310. FIG. 13 shows tri-port crossbar 1320 in which shaft 1340 is perpendicular to the plane of the tri-port crossbar 1320 of the junction and an inflatable Y-shaped-curved element is oriented out of the plane of the crossbar. Shaft 1340 is perpendicular to the Y-shaped tri-port crossbar 1320. One curved inflatable toroid 1310 is oriented out of the plane of the crossbar 1320 via ends 1320*a*, 1320*b*, and 1320*c*. The toroid 1310 has three arms, the ends of which 1310*a*, 1310*b*, and 1310*c* envelop ends 1320*a*, 1320*b*, and 1320*c* of the tri-port crossbar 1320.

EXAMPLE 1

Figure 14:
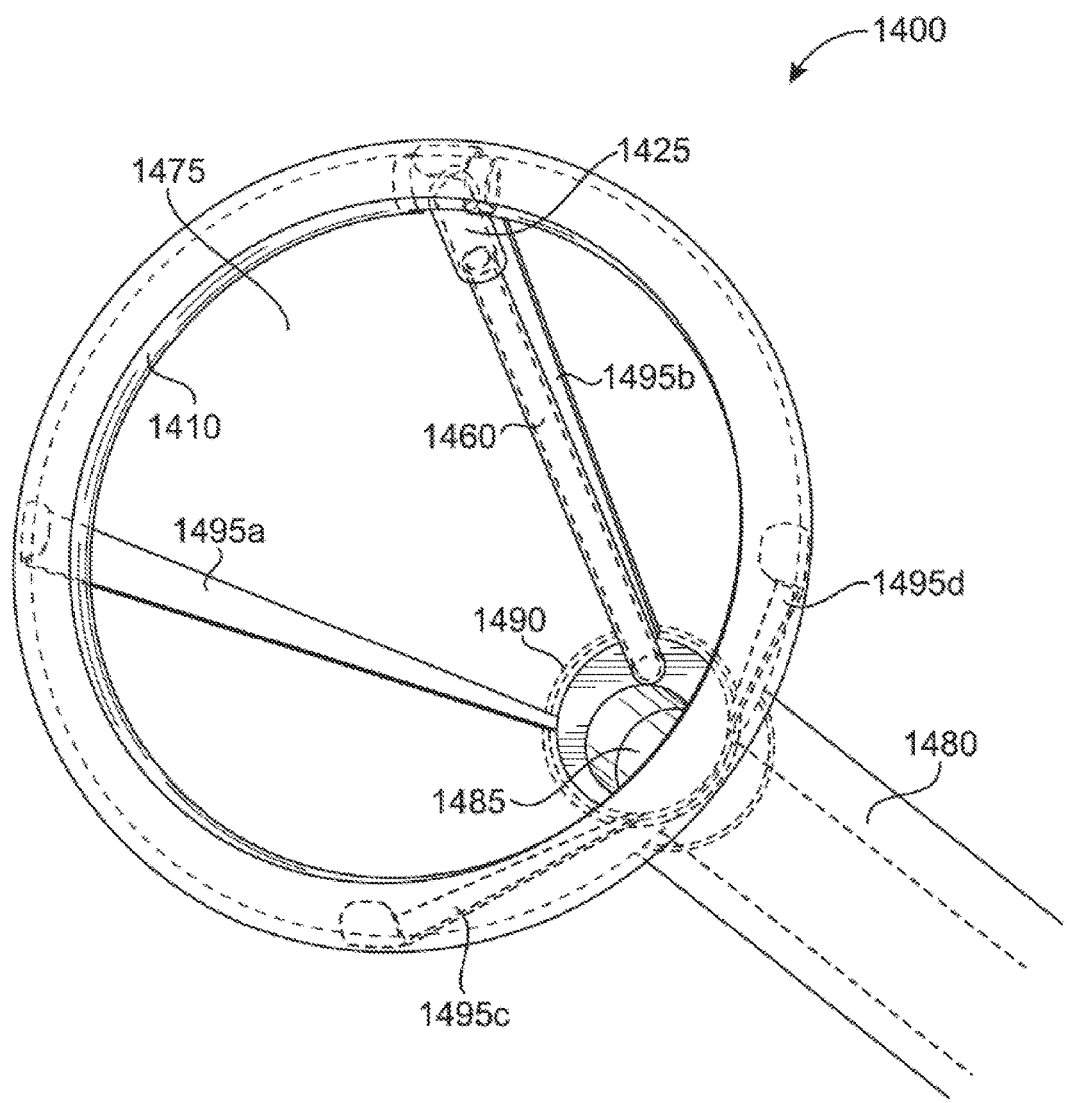
FIG. 14 shows a medical device incorporating a T junction.

In a preferred exemplary embodiment, an inflatable medical device 1400 is prepared as shown in FIG. 14. The inflatable, expandable device includes inflatable toroid 1410 connected to the crossbar ends of T junction 1425. Toroid 1410 is inflatable via inflation lumen 1460 which is connected to the shaft of T junction 1425. Supporting catheter 1480 is used to stabilize the inflatable toroid 1410. Crown 1490 is positioned at one end of catheter 1480 and includes supporting fingers 1495*a*, 1495*b*, 1495*c*, and 1495*d* extending from the crown 1490 to the inflatable toroid 1410. Non-porous membrane 1475 extends from the outer circumference of the inflatable toroid 1410, along the exterior of the metallic fingers 1495*a*, 1495*b*, 1495*c*, and 1495*d* down to the crown 1490 creating a funnel-shaped form. When deployed in a vessel, material (such as emboli) may be gathered within the funnel and channeled down central lumen 1485 of catheter 1480.

In this example, the T junction 1425 is preferably made of polycarbonate. Inflation lumen 1460 is preferably made of polyimide (available from DuPont as KAPTON®) and non-porous membrane 1475 is preferably made of polyurethane (available from Lubrizol as PELLETHANE®). Toroid 1410 preferably comprises polyethylene terephthalate. Metallic crown 1490 and metallic fingers 1495*a*, 1495*b*, 1495*c*, and 1495*d* are preferably formed of 304 grade stainless steel. The components of the medical device are assembled with UV-curable glue (such as that available from Dymax under the 204-CTH series). Supporting catheter 1480 is preferably constructed of PEBAX® polyether block amide with an embedded stainless steel braid for added column strength. Radiopaque marker bands are preferably integrated in the catheter shaft to facilitate fluoroscopic visualization.

The inflatable toroid of this Example is inflated using saline with dilute contrast medium to assist with placement of the medical device within a patient's blood vessel. The entire uninflated device is deployed within a patient's blood vessel from within a guide catheter, preferably a 14 French gauge guide catheter. The device, in its uninflated and collapsed state, may be advanced within or through the lumen of a patient's blood vessel through a sheath introducer and optionally over a guidewire. After the device is inflated and utilized, toroid 1410 is deflated to facilitate withdrawal of the device. Once deflated, the device may be withdrawn back into the 14 French gauge guide catheter and the entire assembly may be withdrawn from the vessel.

EXAMPLE 2

Figure 15:
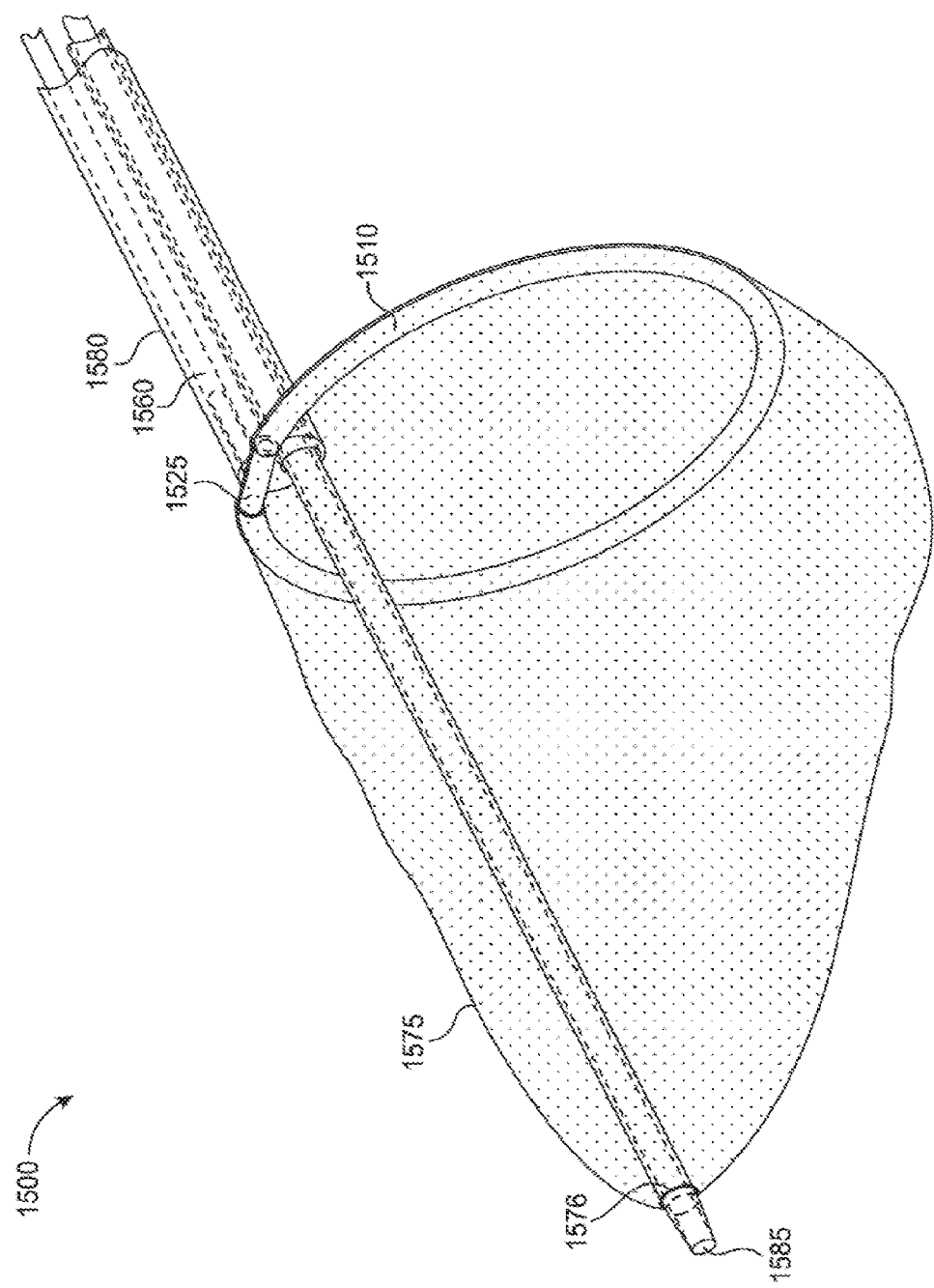
FIG. 15 shows a medical device incorporating a T junction.

In a preferred exemplary embodiment, an inflatable medical device 1500 is prepared as shown in FIG. 15. The inflatable, expandable device includes inflatable toroid 1510 connected to the crossbar ends of T junction 1525. Toroid 1510 is inflatable via inflation lumen 1560 which is connected to the shaft of T junction 1525. Supporting catheter 1580 is used to stabilize the inflatable toroid 1510. Non-porous membrane 1575 extends from the outer circumference of the inflatable toroid 1510, along towards the tip of central catheter tube 1585 and is coupled around catheter tube 1585 at 1576 forming a net. Central catheter tube 1585 extends from the end of the catheter and through membrane 1575; as shown in FIG. 15, membrane 1575 is coupled to catheter tube 1585 at a point distal from the T junction 1525. Central catheter tube 1585 features a lumen to support the use of an optional guidewire. When the device is inflated and deployed in a vessel, material (such as emboli, kidney stones, gallstones, or foreign bodies) may be gathered within the net to be removed from the vessel. The toroid may then be deflated to securely capture the internal material and the entire device may be removed from the vessel. In an alternative embodiment, an optional drawstring filament or filaments may be associated with the membrane 1575 net and/or toroid 1510 to allow the net and/or toroid to be collapsed.

In this example, the T junction 1525 is preferably made of polycarbonate. Non-porous membrane 1575 is preferably made of flexible, non-porous latex. Toroid 1510 preferably comprises polyethylene terephthalate. The components of the medical device are assembled with UV-curable glue (such as that available from Dymax under the 204-CTH series). Supporting catheter 1580 is preferably constructed of PEBAX® polyether block amide with an embedded stainless steel braid for added column strength. Radiopaque marker bands are preferably integrated in the catheter shaft to facilitate fluoroscopic visualization.

The inflatable toroid of this Example is inflated using saline with dilute contrast medium to assist with placement of the medical device within a patient's blood vessel. The entire uninflated device is deployed within a patient's blood vessel, or other parts of the anatomy, from within an appropriately sized guide catheter (preferably a 14 French gauge guide catheter). The device, in its uninflated and collapsed state, may be advanced within or through the lumen of a patient's blood vessel, or other tubular structures within the body, through a sheath introducer and optionally over a guidewire. After the device is inflated and target material has been captured within membrane 1575, the toroid 1510 is deflated to capture the internal material. Once deflated, the device (with captured material) may be withdrawn back into the appropriately sized (e.g., 14 French gauge) guide catheter and the entire assembly may be withdrawn from the patient's body.

EXAMPLE 3

Figure 16A:
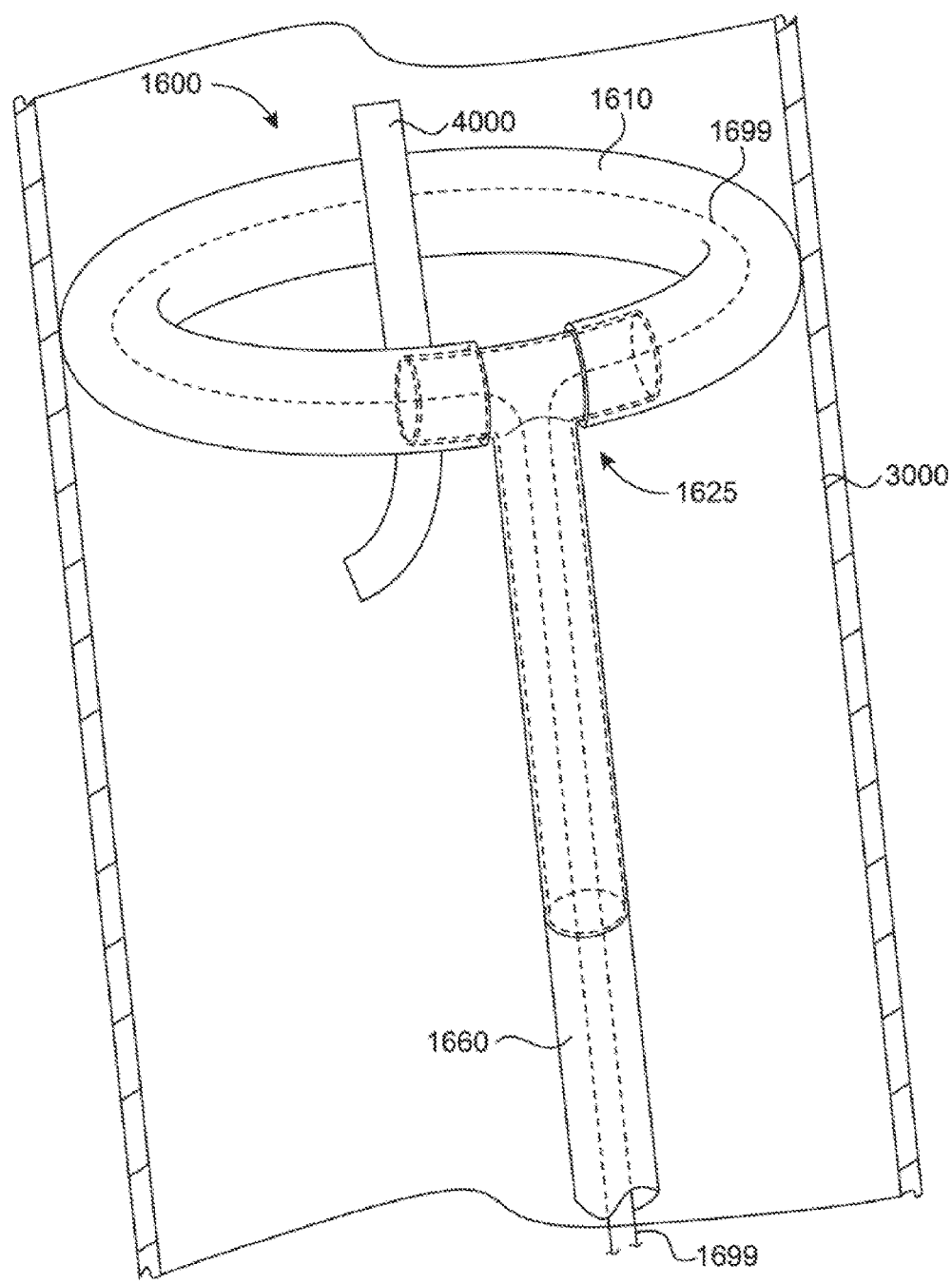
FIG. 16A shows an inflated snare device incorporating a T junction in which the plane of the inflated toroid is perpendicular to the direction of the inflation lumen.

In a preferred exemplary embodiment, inflatable medical device 1600 is prepared as shown in FIG. 16A (similar to the device shown in FIG. 1). The inflatable, expandable device includes inflatable toroid 1610 connected to the crossbar ends of T junction 1625. Toroid 1610 is inflatable via inflation lumen 1660 which is connected to the shaft of T junction 1625. Supporting catheter (not depicted) is coupled to and in fluid communication with inflation lumen 1660. Drawstring filament 1699 has two ends (not depicted) and is threaded up through the catheter, up through the inflation lumen, up through the T junction shaft, out the first end of the crossbar, through the toroid, in the second end of the crossbar, back down through the T junction shaft, back down the inflation lumen, and back down the catheter. At least one end of drawstring filament 1699 is accessible by the user of the device at a point outside of the vessel (3000) where at least one end of the drawstring may be drawn to assist with closure of the toroid mouth around a target object. The second end of drawstring 1699 may also be accessible by the user of the device at a point outside the vessel (so that tension on one or both ends of the drawstring will assist with closure) or the second end of drawstring 1699 may instead be mounted within the device (for example in the T junction) or catheter such that tension on the first end of the drawstring will assist with closure.

When the device is inflated and deployed in a vessel, the inflated toroid is maintained in a plane perpendicular to that of the shaft of the T junction. This orients the central axis of the inflated toroid in the same direction as the axis of the vessel and permits capture of target material (such as foreign bodies) depicted as catheter fragment 4000. When the toroid encircles the target material, the toroid may be deflated and capture of the target material is assisted by operating the drawstring.

The inflatable toroid of this Example is inflated using saline with dilute contrast medium to assist with placement of the medical device within a patient's blood vessel. The entire uninflated device is deployed within a patient's blood vessel as described in Example 1. After the device is inflated and target material is positioned inside the mouth of toroid 1610, the toroid 1610 is deflated and drawstring 1699 is pulled to capture the target material shown in FIG. 16B.

Figure 16B:
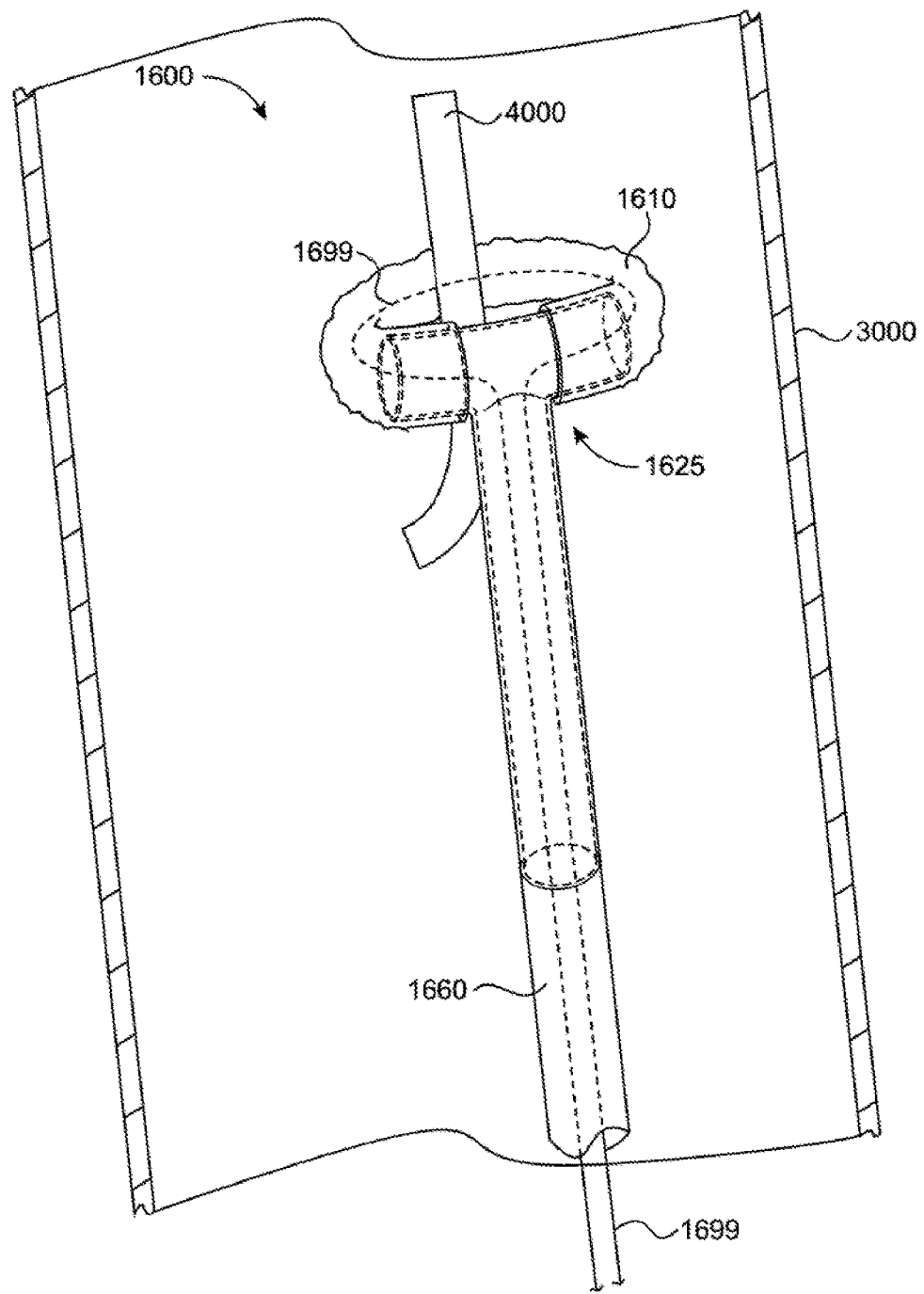
FIG. 16B shows a deflated snare device of 16A capturing a target object.

FIG. 16B shows the device of FIG. 16A in a deflated and collapsed state having ensnared a target material. Once deflated, the device (with captured target material) may be withdrawn back into an appropriately sized (e.g., 14 French gauge) guide catheter and the entire assembly may be withdrawn from the patient's body.

In this example, the T junction 1625 is preferably made of polycarbonate. Toroid 1610 preferably comprises polyethylene terephthalate. The components of the medical device are assembled with UV-curable glue (such as that available from Dymax under the 204-CTH series). Supporting catheter (not depicted) is preferably constructed of PEBAX® polyether block amide with an embedded stainless steel braid for added column strength. Radiopaque marker bands are preferably integrated in the catheter shaft to facilitate fluoroscopic visualization.

EXAMPLE 4

Figure 17:
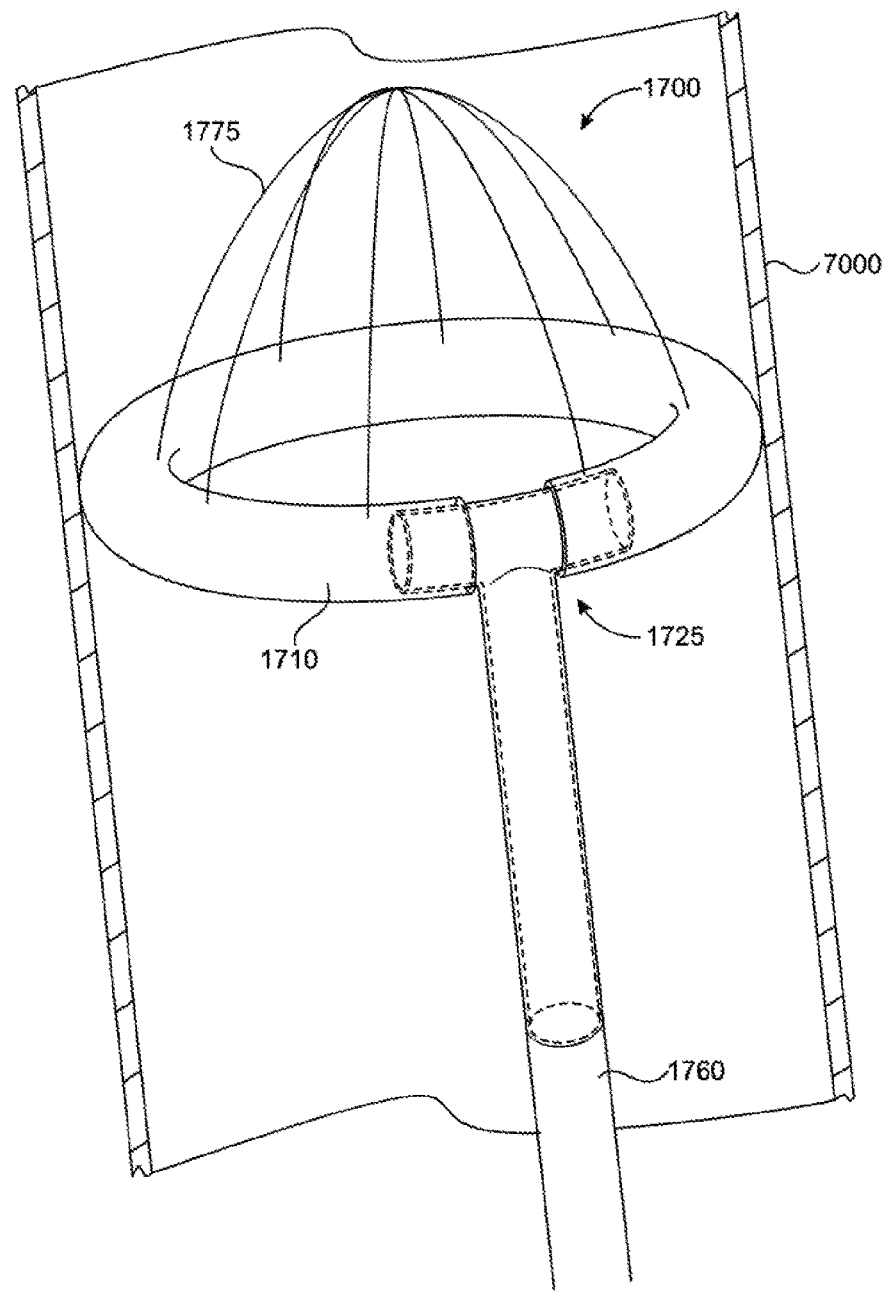
FIG. 17 shows a filter device incorporating a T junction.

In a preferred exemplary embodiment, inflatable filter device 1700 is prepared as shown in FIG. 17 (similar to the device shown in FIG. 1). The inflatable device includes inflatable toroid 1710 connected to the crossbar ends of T junction 1725. Toroid 1710 is inflatable via inflation lumen 1760 which is connected to the shaft of T junction 1725. Supporting catheter (not depicted) is coupled to, and in fluid communication with, inflation lumen 1760. Filter element 1775 is comprised of individual filaments extending from the outer circumference of the inflatable toroid 1710 forming a net to capture target material.

When the device is inflated and deployed in a vessel (depicted here in the inferior vena cava, exterior wall 7000) the inflated toroid is maintained in a plane perpendicular to that of the shaft of the T junction. This orients the central axis of the inflated toroid in the same direction as the axis of the vessel and permits capture of target material (such as emboli).

The inflatable toroid of this Example is inflated using saline with dilute contrast medium to assist with placement of the medical device within a patient's blood vessel. The entire uninflated device is deployed within a patient's blood vessel as described in Example 1. After the device is inflated and emboli have been captured, the toroid 1710 is deflated. Once deflated, the device (with emboli) may be withdrawn back into the appropriately sized (e.g., 14 French gauge) guide catheter and the entire assembly may be withdrawn from the patient's body.

In this example, the T junction 1725 is preferably made of polycarbonate. Toroid 1710 preferably comprises polyethylene terephthalate. The components of the medical device are assembled with UV-curable glue (such as that available from Dymax under the 204-CTH series). Supporting catheter (not depicted) is preferably constructed of PEBAX® polyether block amide with an embedded stainless steel braid for added column strength. Radiopaque marker bands are preferably integrated in the catheter shaft to facilitate fluoroscopic visualization. Filter element 1775 preferably comprises polyester filaments.

In view of the above, it will be seen that the several advantages of the disclosure are achieved and other advantageous results attained. As various changes could be made in the above devices and methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

While various embodiments have been described above, it should be understood that such disclosures have been presented by way of example only, and are not limiting. Thus, the breadth and scope of the subject methods, devices, and systems should not be limited by any of the above-described exemplary embodiments, but should be defined only in accordance with the following claims and their equivalents.

Having now fully described the subject methods, devices, and systems, it will be understood by those of ordinary skill in the art that the same can be performed within a wide and equivalent range of conditions, formulations and other parameters without affecting their scope or any embodiment thereof. All cited patents, patent applications and publications are fully incorporated by reference in their entirety.

What is claimed is:

1. A medical device comprising:
   a. a hollow T-shaped junction of a rigid material, the T-shaped junction comprising a crossbar with a first end and a second end fluidly connected to a shaft;
   b. an inflatable member having a first shape in an uninflated state and having a second shape of a toroid in an inflated state, the inflatable member having a first end and a second end, where the first end of the inflatable member is coupled to the first end of the crossbar and where the second end of the inflatable member is coupled to the second end of the crossbar; and
   c. an inflation lumen having a first end and a second end, where the first end of the inflation lumen is coupled to the shaft and where the second end of the inflation lumen is coupled to a catheter.

2. A medical device of claim 1 further comprising a conical-shaped membrane coupled to the inflatable member.

3. A medical device of claim 2 where the membrane has a first edge and second edge, and each of the first edge and the second edge has a circumference, where the first edge of the membrane has a circumference that is larger than the circumference of the second edge of the membrane.

4. A medical device of claim 3 where the first edge of the membrane is coupled to the inflatable member and the second edge of the membrane is coupled to the catheter.

5. A medical device of claim 2 where the membrane comprises polyurethane.

6. A medical device of any of claim 1, 2 or 5 where the T-shaped junction comprises polyethylene terephthalate.

7. A medical device of claim 4 further comprising a plurality of rigid arms extending from the catheter to the inflatable member.

8. A medical device of claim 4 where the membrane comprises polyurethane and where the T-shaped junction comprises polyethylene terephthalate.

9. A medical device of claim 4 where the second edge of the membrane is coupled to the catheter at a point distal to the T-shaped junction.

10. A medical device of claim 4 where the second edge of the membrane is coupled to the catheter at a point proximal to the T-shaped junction.

11. A medical device of claim 2 where the membrane is non-porous.

12. A medical device of claim 2 where the membrane is porous.

13. A medical device of claim 1 where the toroid is oriented in a plane perpendicular to the direction of the shaft when the inflatable member is in an inflated state.

14. A medical device of claim 1 where the second end of the inflation lumen is selectively detachable from the catheter.

15. A medical device of claim 1 where the second end of the inflation lumen is fixed to the catheter.

16. A medical device of claim 1 where the inflatable member has a third shape in a deflated state.

17. A medical device comprising:
a rigid junction comprising a shaft in fluid communication with a crossbar with a lumen extending therethrough, wherein the rigid junction is fluidly connected to a toroid inflatable between an uninflated first state and an inflated second state, where the toroid is coupled to the crossbar.

18. A medical device of claim 17 where the rigid junction is T-shaped.

19. A medical device of claim 17 where the shaft is perpendicular to and in the same plane as the crossbar.

20. A medical device of claim 17 where the toroid in its inflated second state is oriented in a plane that is perpendicular to the direction of the shaft of the rigid junction.

21. A medical device of claim 17 where the toroid in its inflated second state is oriented in a plane that is:
  a. oriented at an angle greater than or equal to 90 degrees with respect to the direction of the shaft; and
  b. oriented at an angle less than or equal to 180 degrees with respect to the direction of the shaft.

22. A medical device of claim 17 where the rigid junction comprises a metal.

23. A medical device of claim 17 where the rigid junction comprises a polymeric material.

24. A medical device of claim 23 where the rigid junction comprises polyethylene.

25. A medical device of claim 23 where the rigid junction comprises polyethylene terephthalate.

26. A medical device of claim 17 further comprising a conical-shaped membrane coupled to the inflatable member.

27. A medical device of claim 19 where the toroid in its inflated second state is oriented in a plane that is perpendicular to the direction of the shaft of the rigid junction.

28. A medical device of claim 27 wherein the toroid in its inflated second state is not supported by additional structure apart from the crossbar.

* * * * *